US011416123B2

(12) United States Patent
Pandolfi et al.

(10) Patent No.: US 11,416,123 B2
(45) Date of Patent: Aug. 16, 2022

(54) FIRMWARE DESIGN FOR FACILITY NAVIGATION, AND AREA AND LOCATION DATA MANAGEMENT OF PARTICLE SAMPLING AND ANALYSIS INSTRUMENTS

(71) Applicant: Particle Measuring Systems, Inc., Boulder, CO (US)

(72) Inventors: Daniele Pandolfi, Boulder, CO (US); Matt Michaelis, Boulder, CO (US); Paul B. Hartigan, Boulder, CO (US); Cliff Ketcham, Boulder, CO (US)

(73) Assignee: PARTICLE MEASURING SYSTEMS, INC., Boulder, CO (US)

(*) Notice: Subject to any disclaimer, the term of this patent is extended or adjusted under 35 U.S.C. 154(b) by 620 days.

(21) Appl. No.: 16/394,931

(22) Filed: Apr. 25, 2019

(65) Prior Publication Data

US 2019/0250785 A1  Aug. 15, 2019

Related U.S. Application Data

(63) Continuation-in-part of application No. 14/645,853, filed on Mar. 12, 2015, now abandoned.

(60) Provisional application No. 61/953,315, filed on Mar. 14, 2014.

(51) Int. Cl.
*G06F 3/0484* (2022.01)
*G06F 3/0482* (2013.01)
*G01N 33/00* (2006.01)
*G01C 21/20* (2006.01)
*G01N 1/22* (2006.01)
*G01N 15/00* (2006.01)
*G06F 3/0488* (2022.01)
*G01N 35/00* (2006.01)
*G01N 1/02* (2006.01)
*G06F 3/04842* (2022.01)

(52) U.S. Cl.
CPC ......... *G06F 3/0484* (2013.01); *G01C 21/206* (2013.01); *G01N 1/2208* (2013.01); *G01N 1/2226* (2013.01); *G01N 1/2273* (2013.01); *G01N 15/00* (2013.01); *G01N 33/0062* (2013.01); *G06F 3/0482* (2013.01); *G01N 2001/021* (2013.01); *G01N 2001/2223* (2013.01); *G01N 2035/0091* (2013.01); *G01N 2035/00831* (2013.01); *G06F 3/0488* (2013.01); *G06F 3/04842* (2013.01)

(58) Field of Classification Search
CPC ............... G01N 33/0062; G01N 2035/00831
See application file for complete search history.

(56) References Cited

U.S. PATENT DOCUMENTS 4,499,377 A    2/1985   Presser
2003/0105546 A1  6/2003   Robinson et al.
2004/0025604 A1  2/2004   Call et al.
2008/0148816 A1* 6/2008   Groves .............. G01N 15/0227
                                                    73/31.01
2008/0204221 A1  8/2008   Elderkin et al.
2008/0281528 A1  11/2008  Relle, Jr.
2011/0252897 A1  10/2011  Swenson et al.
2013/0105566 A1  5/2013   Calio et al.
2014/0053586 A1  2/2014   Poecher et al.
2014/0060155 A1  3/2014   Hering et al.
2014/0095074 A1  4/2014   Covely et al.
2015/0168457 A1  6/2015   Nakajima et al.
2015/0259723 A1  9/2015   Hartigan et al.
2016/0256097 A1  9/2016   Manautou et al.

FOREIGN PATENT DOCUMENTS

WO  WO 2003/081212   10/2003
WO  WO 2015/138681    9/2015
WO  WO 2018/165590    9/2018

OTHER PUBLICATIONS

Extended European Search Report, dated Dec. 14, 2020, corresponding to European Patent Application No. 20171044.9, 13 pages.
Partial European Search Report and Provisional Opinion, dated Sep. 8, 2020, corresponding to European Patent Application No. 20171044.9, 15 pp.
Azbil Biovigilant (2012) "Investigations 1: Introduction and IMD-A Technology and Features," available at https://biovigilant.com/wp-content/uploads/2018/11/Investigations-1.pdf, 4 pp.
Azbil Biovigilant (2018), "Real-Time Process Control for Healthy, High-Purity Water Systems," available at https://biovigilant.com/wp-content/uploads/2018/11/PT0418-BioVigilant-Webinar-Exec-Summary-F-W.pdf, downloaded from the Internet on Oct. 7, 2019, 7 pp.
Beckman Coulter, "MET One Facility Monitoring System (FMS) Software," available at https://www.beckman.com/air-particle-counters/facility-monitoring-system/software, downloaded from the Internet on Oct. 7, 2019.
Beckman Coulter, "MET One HHPC+ Series," available at https://www.beckman.com/air-particle-counters/met-one-hhpc-plus-series, downloaded from the Internet on Oct. 7, 2019.
Beckman Coulter (2017), "Multisizer 4E Coulter Counter for Quality Control: High resolution sizing, counting and size distribution of cells, particles or sub-visible particles," available at https://media.beckman.com/-/media/pdf-assets/brochures/coulter-counter-multisizer-4e-quality-control-flyerc-201706.pdf, downloaded from the Internet on Oct. 7, 2019, 2 pp.

(Continued)

*Primary Examiner* — Christopher Adam Hixson
(74) *Attorney, Agent, or Firm* — Leydig, Voit & Mayer, Ltd.

(57) ABSTRACT

Provided herein are methods and devices that allow for efficient management of many different sampling locations within a facility. A method for operating a biological sampler, a particle counter, and like air sampling, analysis, and/or monitoring equipment or instrumentation is described, such as by sampling an environment at a sampling position with the biological sampler and storing sample data and other useful information in memory in association with unique identifier(s) including sampling location(s) for the samples. Also provided are associated devices for carrying out the methods.

16 Claims, 24 Drawing Sheets

(56) References Cited

OTHER PUBLICATIONS

Climet Instruments Company, "DataPro 2.5e," available at http://www.climet.com/software/dp25e/index.html, downloaded from the Internet Oct. 7, 2019.
Climet Instruments Company, "DataPro 2.5e Software," available at http://www.climet.com/software/dp25e/index1.html, downloaded from the Internet on Oct. 7, 2019.
Kanomax (2012), "Portable Particle Counter User's Manual: Model 3910," available at https://www.kanomax-usa.com/wp-content/uploads/2015/10/3910_Manual.pdf, 87 pp.
Kanomax (Sep. 2015) "Uploading a Facility Map to Portable Particle Counters," available at https://www.kanomax-usa.com/uploading-a-facility-map-to-portable-particle-counters/.
Kanomax (Apr. 2018) "Versatile Cleanroom Monitoring," available at https://www.kanomax-usa.com/uploading-a-facility-map-to-portable-particle-counters-2/.
Lighthouse Worldwide Solutions, "LMS Express," available at https://www.golighthouse.com/en/real-time-monitoring-systems/lms-express, downloaded from the Internet on Oct. 7, 2019.
Lighthouse Worldwide Solutions, "LMS Pharma," available at https://www.golighthouse.com/en/real-time-monitoring-systems/lms-pharma downloaded from the Internet on Oct. 7, 2019.
Lighthouse Worldwide Solutions, "LMS Pro," available at https://www.golighthouse.com/en/real-time-monitoring-systems/lms-pro, downloaded from the Internet on Oct. 7, 2019.
Particles Plus (Apr. 2015) "3000 Series Unveiled at ESTECH 2015," available at https://particlesplus.com/3000-series-unveiled-at-estech-2015/.
Particles Plus (Jun. 2016) "Advancements in Interface and Communications for Particle Counters," available at https://particlesplus.com/advancements-interface-communications-particle-counters/.
Particles Plus, "Why Particles Plus?" available at https://particlesplus.com/why-particles-plus/, downloaded from the Internet Oct. 7, 2019.
Scott (Oct. 2014), "Instantaneous Microbial Detection for Water: Real-time bioburden monitoring promotes risk reduction and process control," available at https://biovigilant.com/wp-content/uploads/2018/11/CEOctober2014InstantaneousMicroDetectionWater.pdf, downloaded from the Internet on Oct. 7, 2019, 12-14.
Shimadzu Global Analytical and Measuring Instruments, "iSpect DIA-10: Dynamic Particle Image Analysis System," available at https://www.shimadzu.com/an/powder/ispect.html, downloaded from the Internet on Oct. 7, 2019.
Shimadzu Global Analytical and Measuring Instruments, "Particle Size Analysis," available at https://www.shimadzu.com/an/powder/index.html, downloaded from the Internet Oct. 8, 2019.
Shimadzu Global Analytical and Measuring Instruments, "SALD-2300: Laser Diffraction Particle Size Analyzer," available at https://www.shimadzu.com/an/powder/sald2300/2300.html, downloaded from the Internet on Oct. 8, 2019.
Shimadzu Scientific Instruments (2018), "Analyzing Flavor Scientifically: Analytical and Testing Instruments for Food Development," available at https://www.ssi.shimadzu.com/sites/ssi.shimadzu.com/files/Industry/Literature/analytical-and-testing-instruments-for-food-development.pdf, downloaded from the Internet on Oct. 7, 2019, 20 pp.
Shimadzu Scientific Instruments (2015), "Contributing to Improved CFRP Performance and Reliability: CFRP Analysis, Testing and Inspection Evaluation Instruments," available at https://www.ssi.shimadzu.com/sites/ssi.shimadzu.com/files/Industry/Literature/C10G-E037.pdf, downloaded from the Internet on Oct. 7, 2019, 20 pp.
Shimadzu Scientific Instruments (2013), "Solutions for Plastic Evaluation," available at https://www.ssi.shimadzu.com/sites/ssi.shimadzu.com/files/Industry/Literature/C10G-E035.pdf, downloaded from the Internet on Oct. 7, 2019, 54 pp.
TSI Incorporated, "AIRPRO Mobile," available at https://www.tsi.com/products/ventilation-test-instruments/airpro-instruments/airpro-mobile/, downloaded from the Internet on Oct. 7, 2019.
TSI Incorporated, "AIRPRO® Solutions," available at https://www.tsi.com/airpro/, downloaded from the Internet on Oct. 7, 2019.
TSI Incorporated, "Noise Indicator NI-100 Series," available at https://www.tsi.com/products/noise-dosimeters-and-sound-level-meters/noise-dosimeters/noise-indicator-ni-100-series/, downloaded from the Internet on Oct. 7, 2019.
U.S. Appl. No. 14/645,853, filed Mar. 12, 2015.
Biotest, APC SmartTouch brochure; available at http://www.cleanroom.net/brochures/APCSmartTouch.pdf; Downloaded from Internet on Apr. 10, 2019.
Biswas et al. (1984) "High-velocity inertial impactors," *Environ. Sci. Technol.* 18(8):611-616.
Lighthouse Worldwide Solutions-Handheld 3016_5016 Operating Manual https://www.mcqill.ca/epi-biostat-occh/files/epi-biostat-occh/particle_counter_lighthouse_2016_user_manual.pdf Downloaded from Internet on Apr. 10, 2019.
International Preliminary Report on Patentability corresponding to International Patent Application No. PCT/US2015/020098, dated Sep. 14, 2016.
International Search Report with Written Opinion corresponding to International Patent Application No. PCT/US2015/020098, dated Jun. 24, 2015.
Kanomax Model 3910 User's Manual available at https://www.kanomax-USA.com/wp-content/uploads/2015/10/3910_Manual.pdf. Downloaded from Internet on Apr. 10, 2019.
Multi-Poiint Monitoring System Software KF-03, Rion Co. Ltd. available at https://www.rion.co.jp/english/product/paricle/assets/k.-03-E.pdf Downloaded from Internet on Apr. 10, 2019.

\* cited by examiner

FIG. 4

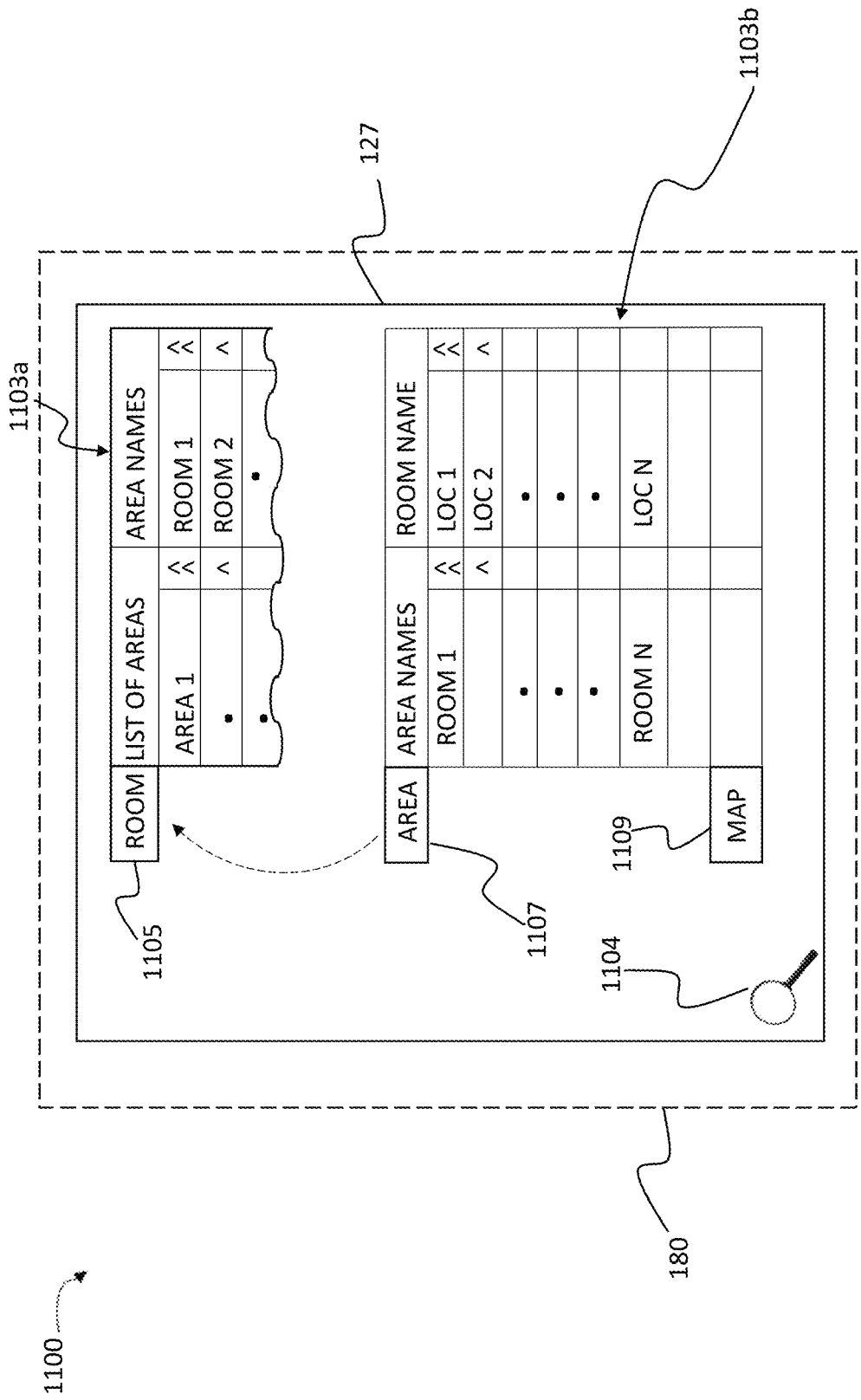

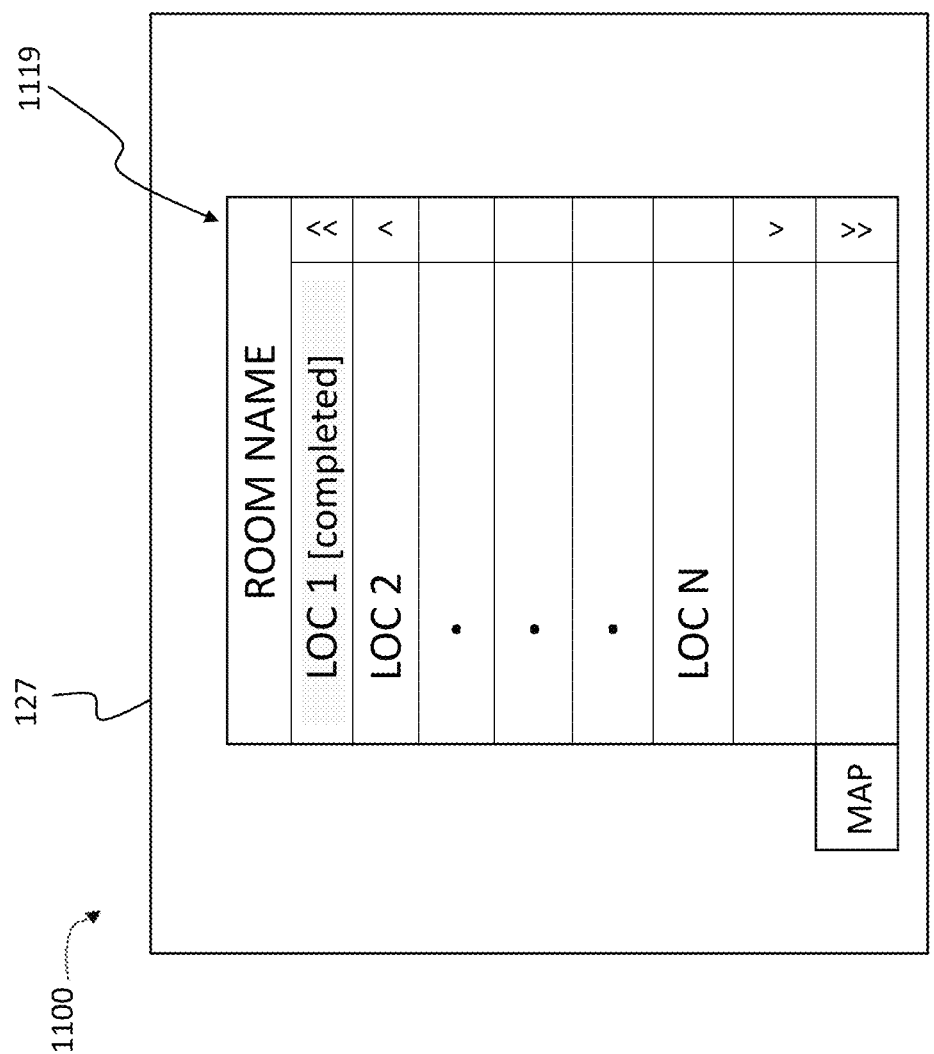

FIRMWARE DESIGN FOR FACILITY NAVIGATION, AND AREA AND LOCATION DATA MANAGEMENT OF PARTICLE SAMPLING AND ANALYSIS INSTRUMENTS

CROSS-REFERENCE TO RELATED APPLICATIONS

This application is a continuation-in-part of U.S. patent application Ser. No. 14/645,853 filed Mar. 12, 2015, which claims the benefit of priority from U.S. Provisional Patent Application No. 61/953,315 filed Mar. 14, 2014, both are which are incorporated by reference herein in their entireties to the extent not inconsistent herewith.

BACKGROUND OF INVENTION

The invention is generally in the field of particle sampling, collection and analysis. The invention relates generally to devices and methods for sampling and characterizing particles in fluids include air and process chemicals (e.g., gases and liquids) for applications including the evaluation of contaminants in a range of cleanroom and manufacturing environments. More specifically, provided are methods and systems that provide for management of many different sampling locations within a facility.

Cleanrooms and clean zones are commonly used in semiconductor and pharmaceutical manufacturing facilities. For the semiconductor industry, an increase in airborne particulate concentration can result in a decrease in fabrication efficiency, as particles that settle on semiconductor wafers will impact or interfere with the small length scale manufacturing processes. For the pharmaceutical industry, where this type of real-time efficiency feedback is lacking, contamination by airborne particulates and biological contaminants puts pharmaceutical products at risk for failing to meet cleanliness level standards established by the Food and Drug Administration (FDA).

Standards for the classification of cleanroom particle levels and standards for testing and monitoring to ensure compliance are provided by ISO 14664-1 and 14664-2. Aerosol optical particle counters are commonly used to determine the airborne particle contamination levels in cleanrooms and clean zones and liquid particle counters are used to optically measure particle contamination levels in process fluids. Where microbiological particles are a particular concern, such as in the pharmaceutical industry, not only is quantification of the number of airborne particles important, but evaluating the viability and identity of microbiological particles is also important. ISO 14698-1 and 14698-2 provide standards for evaluation of cleanroom and clean zone environments for biocontaminants.

Collection and analysis of airborne biological particles is commonly achieved using a variety of techniques including settling plates, contact plates, surface swabbing, fingertip sampling and impactor-based active air samplers. Cascade impactors have traditionally been used for collection and sizing of particles. In these devices, a series of accelerations and inertial impacts successively strip smaller and smaller particles from a fluid flow. Each single stage of an inertial impactor operates on the principle that particles suspended in air can be collected by forcing a dramatic change in the direction of the particle containing airflow, where the inertia of the particle will separate the particle from the airflow streamlines and allow it to impact on the surface. Biswas et al. describe the efficiency at which particles can be collected in a high velocity inertial impactor (*Environ. Sci. Technol.,* 1984, 18(8), 611-616).

In many cleanroom environments, retrieving size information from a particle impactor is not necessary. In this case, a single stage active air sampling impactor system is sufficient to collect biological particle concentrations subject to subsequent detection and analysis. In an impactor-based active air sampler used for collection of biological particles, the impact/collection surface commonly comprises a growth medium, such as an agar plate, as would be used with other biological particle collection techniques. After the particles are collected onto the growth media surface, the media is incubated to allow the biological particles to reproduce. Once the colonies reach a large enough size, they can be identified and characterized, for example using microscopic imaging, fluorescence, staining or other techniques, or simply counted visually by eye or by image analysis techniques.

For these types of biological particle collection and analysis techniques, various operational aspects are important to ensure efficient collection, detection and analysis. For example, the collection efficiency is of critical importance, as failing to detect that biological particles are present in cleanroom air can result in the cleanroom environment having higher levels of contamination than detected. Upon determination that under counting has occurred, pharmaceutical products made in those environments can be identified as failing to meet required standards, potentially leading to costly product recalls. Similarly, failing to ensure that the viability of collected biological particles is maintained during the collection process will also result in under counting. Such a situation can arise, for example, if the collected biological particles are destroyed, damaged or otherwise rendered non-viable upon impact with the growth medium, such that the collected particles do not replicate during the incubation process and, therefore, cannot be subsequently identified.

On the opposite extreme, biological particle concentrations can be overestimated due to false positives. Over counting of this nature arises where a biological particle that is not collected from the cleanroom air, but is otherwise placed in contact with the growth medium, is allowed to replicate during the incubation process and is improperly identified as originating from the cleanroom air. Situations that contribute to false positives include failing to properly sterilize the growth medium and collection system prior to particle collection and improper handling of the growth medium by cleanroom personnel as it is installed into a particle collection system and/or removed from the particle collection system and placed into the incubator. Again, this can result in a pharmaceutical product being identified as failing to meet required standards. Without sufficient measures to identify false positives, such a situation can result in pharmaceutical products that actually meet the required standards, but are destroyed due to an overestimation of biological particle concentration in the cleanroom air indicating that the standards were not met.

There remains a need in the art for particle collection systems capable of achieving efficient sampling of biological particles. For example, particle collection systems are needed for cleanroom and manufacturing applications that provide high particle collection efficiencies while maintaining the viabilities of collected bioparticles. In addition, particle collection systems are needed for cleanroom and manufacturing applications that reduce the occurrence of false positive detection events. There is also a need, particularly for applications requiring a large number of samples, with each sample associated with a specific location in a facility, for managing and tracking of the many different sampling locations within a facility.

SUMMARY OF THE INVENTION

Provided herein are methods and devices for achieving simple and straightforward management of many different sampling locations within a facility. This management can be particularly challenging for applications where there may be hundreds or more of unique sampling locations, and each sampling location having a sample associated therewith.

In one aspect of the disclosure, a method of operating a portable particle sampling device is provided. The method comprises the steps of: sampling an environment at a sampling location with the device; associating the sampling location with a unique identifier, wherein the unique identifier comprises an area and the sampling location; selecting the area; and displaying a sampling location associated with the selected area on a graphical user interface (GUI) connected to the device. In an embodiment, the unique identifier further comprises a room.

In an embodiment, the method further comprises the step of providing the device to a user tasked with sampling a facility at the sampling location, wherein the facility has a plurality of spatial tiers including: a building, the area, and a room. In the embodiment, the method may further comprise the steps of receiving a request from the user for spatial data for one of the plurality of spatial tiers of the facility; and in response to the request, displaying the spatial data to the user to facilitate the user navigating to the sampling location. In the embodiment, the device may comprise a first device and at least a second device, and the method may further comprise exporting at least one of: the spatial data of the facility, a device recipe, and an identifier of the user, from the first to the at least a second device. In the embodiment, the device may comprise a first device and at least a second device, and the method may further comprise importing at least one of: the spatial data of the facility, a device recipe, and an identifier of the user, from the first to the at least a second device.

In another embodiment, the method may further comprise the steps of receiving an indication that the device has arrived at the sampling location; and in response to the indication, loading a device recipe for at least one of: particle sampling, and particle analysis. In the embodiment, the indication may be received from the user via the GUI. In the method according to this embodiment, the step of loading the device recipe may include loading the recipe according to the sampling location corresponding to the indication received. In the embodiment, the device may be provided to the user pre-loaded with at least one recipe for the sampling location(s).

In the embodiment, the associating step may comprise in response to the device sampling and/or analyzing particles of the sampling location, storing sample data for the sampling location in association with: the unique identifier, and the device recipe. For example, the sample data for the sampling location may be stored in association with the unique identifier, and an identifier of the device recipe. In the method according to this embodiment, the sample data may be further stored in association with an identifier of the user (e.g., a username). In the embodiment, the sample data may be further stored in association with a time and date at which the device sampled the environment at the sampling location. The method according to this embodiment may further comprise transmitting the sample data to a location remote from the device for at least one of: monitoring, and archiving, of the sample data.

In yet another embodiment, the method further comprises loading a sampling plan routine corresponding to the sampling of the facility by the user, wherein the device is provided to the user pre-loaded with the sampling plan routine. In the embodiment, the sampling plan routine may include the spatial data of the facility. The method according to this embodiment may further comprise the step of loading user instructions corresponding to the sampling plan routine, wherein the device is provided to the user pre-loaded with the user instructions. The method of the embodiment may comprise the steps of receiving a request from the user for the user instructions for the sampling; determining responsive user instructions for the at least one sampling location; and displaying the responsive user instructions as at least one of: text, and graphics, to the user. The method according to this embodiment may further comprise causing the GUI and the user instructions to be displayed concurrently to the user, or causing the user instructions to be displayed as a portion of the GUI.

In still another embodiment, for the method step of receiving a request from the user for spatial data, the request may be received via the GUI. In the embodiment, the user interacts with the GUI via a touchscreen display of the device. In the method according to this embodiment, the request may be received from the user via a GUI drop-down menu including at least one of: textual, and graphical descriptors, of the plurality of spatial tiers of the facility. In the method of this embodiment, the receiving step may include receiving an indication of which of the textual and/or graphical descriptors was selected by the user from the drop-down menu. In the embodiment, the responsive spatial data may be displayed based on the indication of which of the textual or graphical descriptors were received.

In another embodiment, the method step of displaying the spatial data to the user includes causing responsive spatial data to be displayed as a graphical map to the user. In the embodiment, the graphical may be stored as a standard format image file, for example and without limitation, a jpg file or a png file. The method according to this embodiment may further comprise causing the GUI and the graphical map to be displayed concurrently to the user, or causing the graphical map to be displayed, to the user, as a portion of the GUI. In this embodiment, the step of causing responsive spatial data to be displayed as a graphical map to the user may include displaying a graphical map of the room. In the embodiment, the graphical map may include the sampling location(s).

In yet another embodiment, the method further comprises loading the spatial data corresponding to the plurality of spatial tiers of the facility, wherein the device is provided to the user pre-loaded with the spatial data. In the embodiment, the spatial data may include one or more graphical maps for one or more of the plurality of spatial tiers of the facility. The displaying step according to the embodiment may include displaying the one or more graphical maps to the user, and wherein the one or more graphical maps include at least one or: textual labels, and graphical labels, for the one or more of the plurality of spatial tiers of the facility. In the embodiment, the one or more graphical maps further include at least one of: textual labels, and graphical labels, for the sampling location.

In another aspect of the disclosure, a portable particle sampling device is provided for sampling an environment at a sampling location. The device comprises a device housing including a sampling port; a sampler positioned in the housing and in flow communication with the sampling port; a display visible to a user of the device; and a processor in communication with: the display, the sampler, and at least one memory device positioned at least one of: in or on the device housing, and remote from the device housing. The processor is programmed to: associate the sampling location with a unique identifier, wherein the unique identifier comprises an area and a sampling location; facilitate a user of the device selecting the area; and display a sampling location associated with the selected area on a GUI connected to the device.

In yet another aspect of the disclosure, a non-transitory computer-readable medium (NTCRM) is provided. The NTCRM stores, as software, program instructions which, when executed by one or more processors of, or in communication with, a portable particle sampling device, cause the processor(s) to: associate a sampling location of the device with a unique identifier, wherein the unique identifier comprises an area of a facility and the sampling location; facilitate a user of the device selecting the area; and display the sampling location associated with the selected area on a GUI connected to the device.

In still another aspect of the disclosure, a computer-implemented method of operating a portable particle sampling device for sampling locations in a facility is provided. The facility has a plurality of spatial tiers including: at least one building, at least one area, and at least one room. The computer-implemented method comprises the steps of: providing the device to a user tasked with sampling at least one of the sampling locations in the facility; receiving, by a processor of the device, a request from the user for spatial data for one of the plurality of spatial tiers of the facility stored in a memory in communication with the processor; in response to the request, displaying, by the processor, the spatial data to the user to facilitate the user navigating to the at least one sampling location; receiving, by the processor, an indication that the user has arrived at the at least one sampling location; in response to the indication, loading, by the processor, a device recipe for at least one of: particle sampling, and particle analysis, from the memory; and in response to the device sampling and/or analyzing the particles of the least one sampling location using the recipe, storing, by the processor, particle sample data for the at least one sampling location in the memory in association with identifiers of: the at least one sampling location, and the recipe.

In another aspect of the disclosure, a portable particle sampling device for sampling locations in a facility is provided. The device comprises a device housing including a sampling port; a sampler positioned in the housing and in flow communication with the sampling port; a display visible to a user of the device; and a processor in communication with: the display, the sampler, and at least one memory device positioned at least one of: in or on the device housing, and remote from the device housing. The processor is programmed to: receive a request from a user of the device for spatial data for one of the plurality of spatial tiers of the facility stored in the memory; in response to the request, display the spatial data to the user to facilitate the user navigating to at least one of the sampling locations; receive an indication that the user has arrived at the sampling location(s); in response to the indication, load a device recipe for at least one of: particle sampling, and particle analysis, from the memory; and in response to the device sampling and/or analyzing the particles of the sampling location(s) using the recipe, store particle sample data for the sampling location(s) in the memory in association with identifiers of: the sampling location(s), and the recipe.

In yet another aspect of the disclosure, the method is for operating a biological sampler by sampling an environment at a sampling position with the biological sampler and associating the sampling position with a unique identifier, wherein the unique identifier comprises an area and a location. Any of the methods, systems and devices provided herein is an integrated method or unit. Such integration is beneficial in terms of sampling management and control, avoiding separate components that must both be moved together and/or connected to each other.

In this manner, a user operating a portable biological sampler may rapidly proceed from sampling position to sampling position taking samples and save time by being able to rapidly access the unique identifier associated with each sampling position, in a rapid, uniform and integrated manner.

For example, the sampling position may be pre-selected and the unique identifier of the sampling position pre-loaded into the biological sampler. This refers to the situation where sampling position is known ahead of time and loaded into the biological sampler. The user of the biological sampler then proceeds to the sampling position and takes the sample.

The methods provided herein, alternatively, are compatible with a user selecting a sampling position and inputting the area and the location of the sampling position into the biological sampler. In this manner, the biological sampler may be considered subsequently pre-set with that input sampling position for later sampling, such as by another user or at a later time and/or date.

In an embodiment, the sampling and associating steps are repeated at a plurality of distinct sampling positions, wherein each sampling position has a unique identifier that is different from a unique identifier of every other sampling position. The methods and devices are compatible with any number of distinct sampling positions. In an aspect, the plurality of distinct sampling positions is greater than or equal to 2 and less than or equal to 1,000.

In an embodiment, the preselected sampling position comprises a plurality of areas, and each area comprises a plurality of locations. In an aspect, the number of areas is selected from a range that is greater than or equal to 2 and less than or equal to 500, and each area is associated with a plurality of locations, wherein the number of locations for each area is independently selected from a range that is greater than or equal to 2 and less than or equal to 500. As the number of sample positions increases, management of associated samples becomes increasingly complicated. The systems and methods provided herein allow rapid selection for sample positions that are associated by area and location. For example, for sample positions that are described as having 10 areas, with each area having 10 locations, selection of an area automatically filters the number of possible sample locations to 10. This is in contrast to conventional samplers where a list of all 100 locations is presented and a user must select one of the 100 locations. This can be a significant resource and time sink with attendant inefficiency. This inefficiency is substantially avoided herein by the association of the sampling position with the unique identifier.

The area and location may correspond to any number of physical locations or descriptors as desired and tailored for the specific application. For example, the area may correspond to a campus, a building, a floor, a process line, or a room. The location may then accordingly correspond to a position within the area. In an aspect, the area corresponds to a room and the location corresponds to a position within the room. In a similar manner, the area may correspond to a process line in a manufacturing application with a first location corresponding to a first sampling position to detect biologicals associated with the process line and a second location corresponding to a second sampling position to detect biologicals in a control location within the process line.

In this manner, as a user enters a room or process line, the area corresponding to the room or process line is provided to the sampler, and the number of possible sample positions accordingly reduced to those having the area associated therewith.

In an aspect, the position is a fixed site within a room.

In an embodiment, the unique identifier comprises at least one additional unique identifier variable that is a sub-location or a supra-area. Such an additional unique identifier variable may be useful to further subdivide the sampling position, such as by floor/room/position; building/room/position; operator/room/position; division/process/position; and the like.

Any of the sampling positions may be labeled to facilitate sampler positioning. The label may be physically observed by a user who can efficiently proceed to the desired position with the sampler. To further improve efficiency, the label may be tagged, wherein the tagging provides automatic identification by the biological sampler of the unique identifier. This may be a label that is bar-coded and read by the sampler, using a radio-frequency identification (RFID) and corresponding reader, or other methods known in the art.

In an embodiment, any of the methods provided herein further comprises the step of identifying the area in which the biological sampler is positioned; and inputting the identified area to the biological sampler data, thereby reducing the number of accessible sampling positions displayed by the biological sampler. In an aspect, the inputting step comprises manual entry by a user of the biological sampler. The inputting step may be further improved by selecting the location from a sampler-displayed list of locations available for the inputted area.

The identifying step may be automated so that a user need not input information directly. In an embodiment, the automated step is selected from the group consisting of: scanning; positioning the sampler in close proximity to a radio frequency identification tag; and tracking a biological sampler position with a positioning receiver connected to the biological sampler. A list of locations associated with the inputted area may be displayed by the biological sampler, and the user can then select from the list.

Any of the methods provided herein may relate to a sampler that has an impact surface for collecting and growing biological particles that have impacted the impact surface. In an embodiment, the sampling comprises exposing an impact surface of the sampler to sample gas; and removing the impact surface from the sampler. As discussed, such sampling that is performed for an individual sampler location becomes difficult to manage when there is a large number of distinct individual sampler locations. The methods provided herein, therefore, are particularly useful for managing such samplers and samples.

In an embodiment, the method further comprises the step of associating the removed impact surface with the unique identifier. In an aspect, the associating the removed impact surface with the unique identifier comprises tagging. The tagging may comprise providing a readable bar code to the impact surface or a container in which the impact surface is confined. In an aspect, the impact surface is an exposed surface of a growth media, such as agar.

Any of the methods provided herein may further comprise the step of observing the growth media for biological growth over a time period and the observing comprises visual detection and/or counting of growth colonies arising from individual viable biological particle impacts with the impact surface.

Any of the methods provided herein may relate to a sampling step that comprises collection of biological particles for a preselected sampling time.

In an embodiment, the method further comprises the step of associating a sample parameter with the unique identifier. Examples of sample parameters include a sample parameter selected from the group consisting of: sampler area; sampler location; a user-provided comment; sample volume; time sampled, sample start date; sample start time; sample end date, sample end time, flow rate; target time; interval; alarms; pauses; an impactor surface serial number; operator identifier; and any combination thereof.

In an aspect, the impactor surface is confined within a container such as a petri dish having the impactor surface serial number.

In an embodiment, the method further comprises generating a report comprising at least one impactor parameter.

Any of the methods provided herein may be for a biological sampler to detect biologics in air samples, including viable biologics. The method may be used in an industry selected from the group consisting of: pharmaceutical manufacture, chemical manufacture; food processing; food manufacturing; and bioterrorism detection.

Any of the methods provided herein may further comprise the steps of: selecting an area; and displaying a list of all possible locations associated with the selected area on a graphical user interface connected to the biological sampler. In an embodiment, the graphical user interface is integrated with the biological sampler.

In still another embodiment, provided herein is a biological sampler for carrying out any of the methods provided herein. The sampler may comprise a sampling head comprising one or more intake apertures for sampling a fluid flow containing biological particles; an impactor base operationally connected to receive at least a portion of the fluid flow from the sampling head; the impactor base comprising an impact surface for receiving at least a portion of said biological particles in the fluid flow and an outlet for exhausting the fluid flow; a processor for storing one or more sampling positions, wherein the sampling position is associated with a unique identifier comprising an area and a location; and a display operably connected to the processor for displaying all locations associated with an area. The display may comprise a graphical user interface to provide user-selection of one of the locations displayed by the display. In this manner, the sampler position may be rapidly selected during use, thereby minimizing user error and increasing management efficiency, particularly for large number of potential sampling locations.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 4 illustrates a report record generated for the sampling position. As desired, any number of sample parameters may be contained in the report record and the sample parameters may be used with the sample to assist in sample management.

FIGS. 11A-11F illustrate screens and operational aspects of a graphical user interface (GUI) presented to users via a display of the device of FIG. 8, according to some embodiments of the disclosure.

DETAILED DESCRIPTION OF THE INVENTION

Figure 1A:
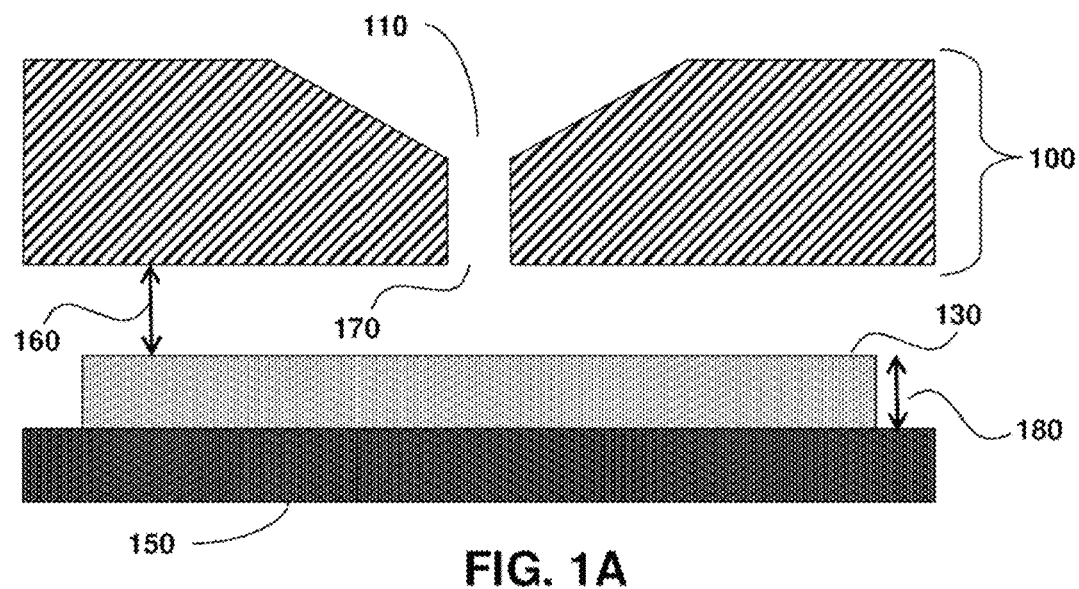
FIG. 1A and FIG. 1B are schematic illustrations of fluid flow components for use with an impact surface of the sampler and corresponding fluid flow with respect to the impact surface.

In general, the terms and phrases used herein have their art-recognized meaning, which can be found by reference to standard texts, journal references and contexts known to those skilled in the art. The following definitions are provided to clarify their specific use in the context of the invention.

"Particle" refers to a small object which is often regarded as a contaminant. A particle can be any material created by the act of friction, for example when two surfaces come into mechanical contact and there is mechanical movement. Particles can be composed of aggregates of material, such as dust, dirt, smoke, ash, water, soot, metal, minerals, or any combination of these or other materials or contaminants. "Particles" may also refer to biological particles, for example, viruses, spores and microorganisms including bacteria, fungi, archaea, protists, other single cell microorganisms and specifically those microorganisms having a size on the order of 1-20 µm. Biological particles include viable biological particles capable of reproduction, for example, upon incubation with a growth media. A particle may refer to any small object which absorbs or scatters light and is thus detectable by an optical particle counter. As used herein, "particle" is intended to be exclusive of the individual atoms or molecules of a carrier fluid, for example, such gases present in air (e.g., oxygen molecules, nitrogen molecules, argon molecule, etc.) or process gases. Some embodiments of the present invention are capable of sampling, collecting, detecting, sizing, and/or counting particles comprising aggregates of material having a size greater than 100 nm, or 10 µm or greater. Specific particles include particles having a size selected from 100 nm to 10 µm or greater.

The expression "sampling a particle" broadly refers to collection of particles in a fluid flow, for example, from an environment undergoing monitoring. Sampling in this context includes transfer of particles in a fluid flow to an impact surface, for example, the receiving surface of a growth medium. Alternatively sampling may refer to passing particles in a fluid through a particle analysis region, for example, for optical detection and/or characterization. Sampling may refer to collection of particles having one or more preselected characteristics, such as size (e.g., cross sectional dimension such as diameter, effective diameter, etc.), particle type (biological or nonbiological, viable or nonviable, etc.) or particle composition. Sampling may optionally include analysis of collected particles, for example, via subsequent optical analysis, imaging analysis or visual analysis. Sampling may optionally include growth of viable biological particles, for example, via an incubation process involving a growth medium. Such growth is a useful indication of viability as well as for assisting in determining presence of biological particles by visual inspection. A sampler refers to a device for sampling particles.

Impactor refers to a device for sampling particles. In some embodiments, an impactor comprises a sample head including one or more intake apertures for sampling a fluid flow containing particles, whereby at least a portion of the particles are directed on to an impact surface for collection, such as the receiving surface of a growth medium (e.g., culture medium such as agar, broth, etc.) or a substrate such as a filter. Impactors of some embodiment, provide a change of direction of the flow after passage through the intake apertures, wherein particles having preselected characteristics (e.g., size greater than a threshold value) do not make the change in direct and, thus, are received by the impact surface. The threshold size value may be selected such as by varying the separation distance between the exit of the intake aperture and the impact surface and/or varying the flow rate through the intake aperture.

The expression "detecting a particle" broadly refers to sensing, identifying the presence of and/or characterizing a particle. In some embodiments, detecting a particle refers to counting particles. In some embodiments, detecting a particle refers to characterizing and/or measuring a physical characteristic of a particle, such as diameter, cross sectional dimension, shape, size, aerodynamic size, or any combination of these. A particle counter is a device for counting the number of particles in a fluid or volume of fluid, and optionally may also provide for characterization of the particles, for example, on the basis of size (e.g., cross sectional dimension such as diameter or effective diameter), particle type (e.g. biological or nonbiological, or particle composition. An optical particle counter is a device that detects particles by measuring scattering, emission or absorbance of light by particles.

"Flow direction" refers to an axis parallel to the direction the bulk of a fluid is moving when a fluid is flowing. For fluid flowing through a straight flow cell, the flow direction is parallel to the path the bulk of the fluid takes. For fluid flowing through a curved flow cell, the flow direction may be considered tangential to the path the bulk of the fluid takes. For laminar flow, flow direction corresponds to the direction of fluid flow streamlines.

"Flow rate" refers to an amount of fluid flowing past a specified point or through a specified area, such as through intake apertures or a fluid outlet of a particle impactor. In one embodiment a flow rate refers to a mass flow rate, i.e., a mass of the fluid flowing past a specified point or through a specified area. In one embodiment a flow rate is a volumetric flow rate, i.e., a volume of the fluid flowing past a specified point or through a specified area. In one embodiment the flow rate may correspond to an average fluid velocity calculated by the volumetric flow rate divided by the cross-sectional area of the fluid conduit in which flow occurs.

Laminar flow refers to a flow that is predictable, steady and not random, in contrast to turbulent flow, and such flows are useful in the devices and methods provided herein to better control impaction of particles satisfying a certain threshold size to improve detection characteristics. Laminar flow refers to flow situations where the ratio of inertial to viscous forces as defined by the Reynolds number ($Re=\rho VD/\mu$; $\rho$ is fluid density, V is average velocity, D is a size of the conduit in which the fluid flows, such as aperture dimension or separation distance, and $\mu$ is the fluid viscosity), is less than about 2000, less than about 1000, less than about 100, or less than about 1.

"Characteristic dimension" refers to a width, diameter, or effective diameter of a flow channel such as an aperture. Effective diameter corresponds to a diameter for a circle having a cross-section area equivalent to the flow channel or aperture.

"Integrated" or "integrated part" is used herein to refer to any of the methods or systems described herein that is incorporated within a single device. This ensures that the methods are reliably and rapidly performed, within the context of a single platform, without additional external components that must be connected to a central unit. Accordingly, any of the processors, displays and/or inputs, outputs and the like are integrally part of the biological sampler or impactor device. For example, the display may be a touch screen display that a user directly controls and that is an integral part of the impactor device. The associating may occur via a processor that is embedded within or is part of the sampler or device, so that any sampling data is associated with a unique identifier that comprises an area and a location. This is in contrast to embodiments wherein an external device is connected, such as via a hardwire connection or wireless connection, to the sampler device.

It may be noted that any reference to elements in the singular may also be construed to relate to the plural and vice-versa without limiting the scope of the disclosure to the exact number or type of such elements unless set forth explicitly in the appended claims.

Example 1: Impactors

Figure 1B:
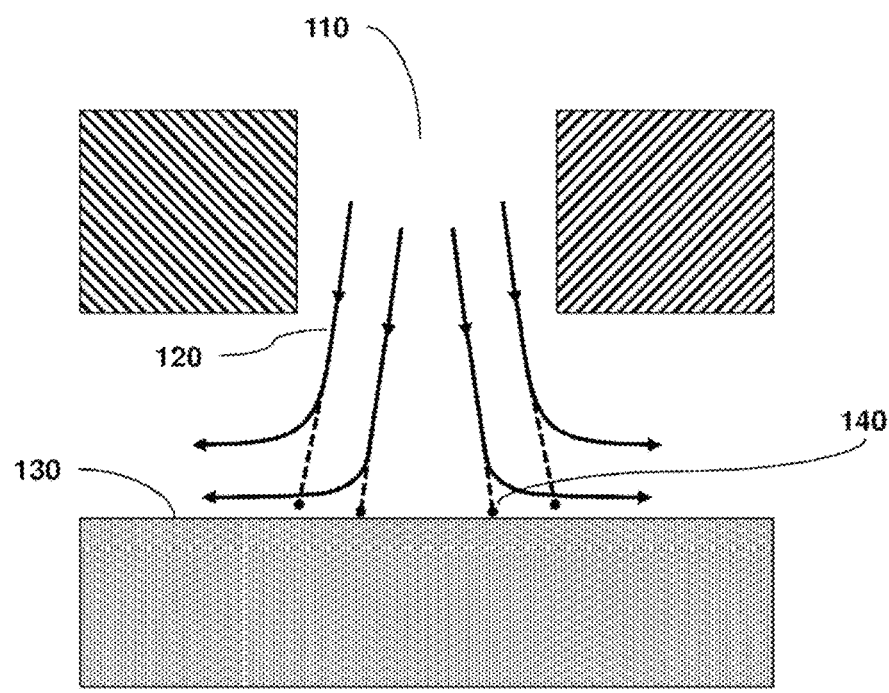

FIG. 1A provides a schematic diagram illustrating the general construction of a particle impactor and FIG. 1B illustrates an expanded view of a particle impactor to further illustrate the operational principal. As shown in these Figures, gas flow is directed through an intake aperture 110 in a sampling head 100 where it is accelerated towards an impact surface 130, which forces the gas to rapidly change direction, following flow paths or streamlines 120 under laminar fluid flow conditions. Due to their momentum, particles 140 entrained in the gas flow are unable to make the rapid change in direction and impact on the impact surface 130. In the embodiment shown in FIG. 1A and FIG. 1B, impact surface 130 is supported by impactor base 150. In embodiments, impact surface 130 comprises the receiving surface of a growth medium, such as agar, provided in a growth medium container or petri dish. Viable biological particles collected on the impact surface, for example, can subsequently be grown and evaluated to provide an analysis of the composition of the fluid flow sampled. For collection of biological particles on the impact surface, control of the separation distance 160, such as a separation distance between the exit 170 of the intake aperture 110 and the impact surface 130, is important. If the distance is too large, for example, the particles may sufficiently follow the fluid path so as to avoid impact with the impact surface. If the distance is too small, however, the particles may impact the impact surface with a force sufficient to render the particles non-viable or otherwise adversely affect the ability of a biological particle to sufficiently reproduce to be visually detected by a user. After sampling, the impact surface is removed and a time period elapsed sufficient for biological particle growth to provide an indication of presence or absence of biological particles. A new impact surface is provided to the sampler for further sampling, such as at another sampling position.

Accordingly, there is a need in the art to manage the sampling, including in view of the potentially very large number of unique sampling positions. Provided herein are methods and devices that assist in sampling management, including by associating each sampling position with a unique identifier. The unique identifier is defined by an area and location tied to the sampling position.

Example 2: Firmware Design for Area and Location Data Management of Biological Air Samples Collected on Media Plates The firmware is structured to allow for simple management of many different sampling locations within a facility.

When samples need to be taken at many locations within a facility the current practice is to either enter a specific location onto a sampler manually every time a sample is taken or to manually track the sample either through the use of external paperwork (or electronic methods), or directly onto the sampling plate.

By creating firmware that structures the samples to be taken into a hierarchal fashion it is possible to identify a specific AREA within a facility for example, Filing Line 1. As well as a specific LOCATION within that area, such as Background Location 1.

Figure 2:
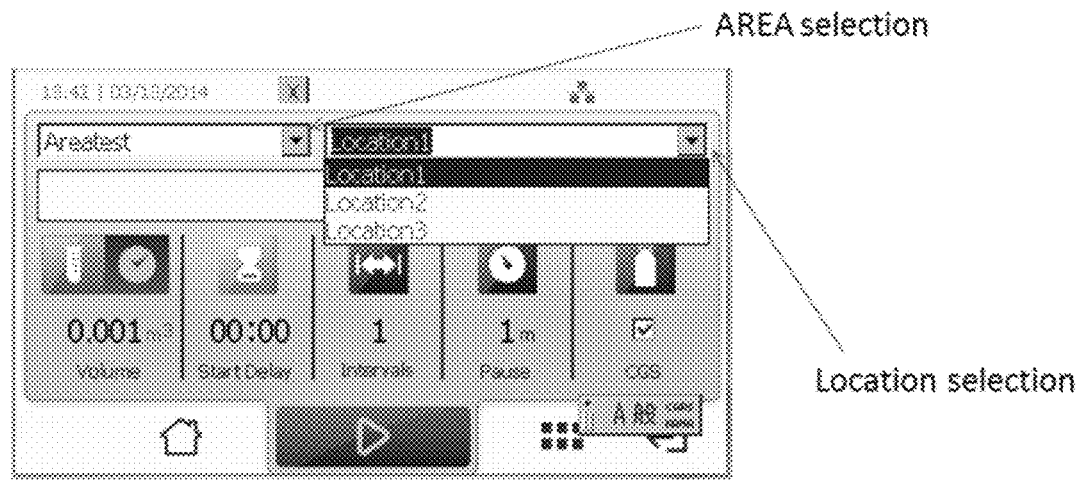
FIG. 2 shows a graphical user interface where the area is selected from the main screen.
Figure 3:
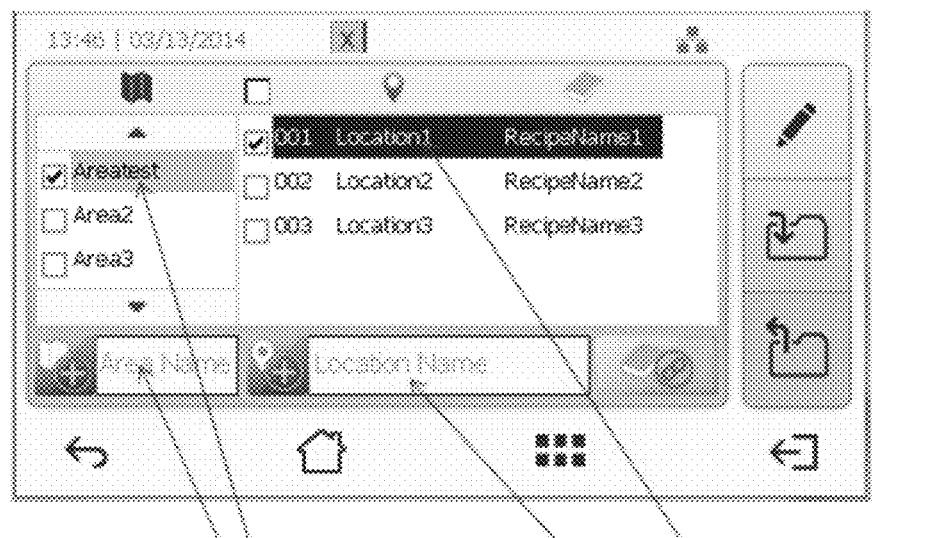
FIG. 3 shows a graphical user interface that, based on the area selection, displays possible locations associated with that area and provides the ability to create additional locations for the area.
Figure 4:
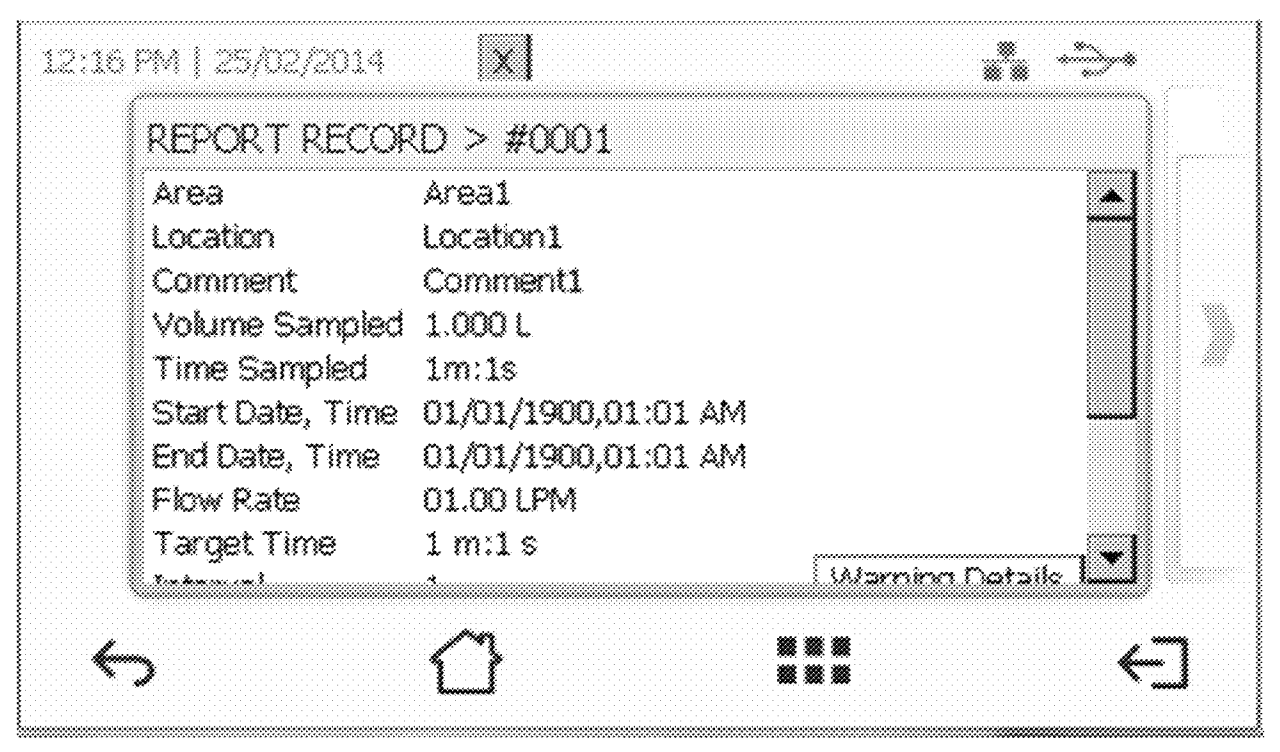
Figure 5:
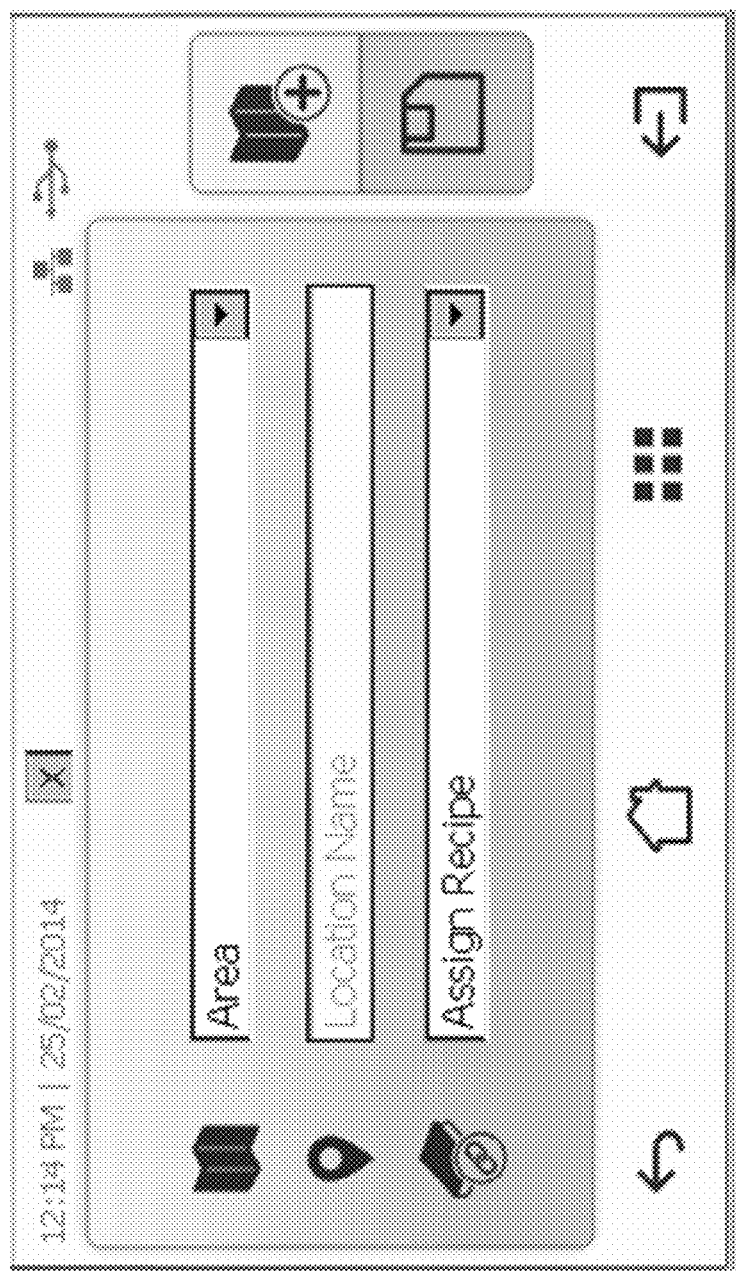
FIG. 5 illustrates an interface for defining unique area/location identifiers along with any other relevant information.

With this type of structure it simplifies the user's selection of the sample point within a particular area and the specific location within that area. This two tiered structure reduces the possibility for error in external recording of the information as well as speeds the ability to identify the proper area and location within that area when taking a sample by having it selectable from a drop down menu. An example is illustrated in FIGS. 2-4, with selection of an area (FIG. 2), corresponding locations associated with that area (FIG. 3), and a generated report record (FIG. 4). FIG. 5 illustrates a user interface to, for example, input a location for a given area and otherwise allow manipulation, variation, and handling of a sampling position.

Existing devices, in contrast, use a single level structure for identification or require manual entry.

Facilities requiring periodic or continual air sampling and monitoring may be large and may require precautions such as gowning by personnel working in areas like cleanrooms. The facilities may span multiple buildings. With experience, personnel conducting air sampling and monitoring of specific areas with facilities develop familiarity with the buildings, areas, and/or rooms they frequent. However, personnel who are new to the facility and/or who are unfamiliar with the layout and floorplans of portions of the facilities requiring air sampling and monitoring may be hindered in their ability to effectively navigate through the areas and rooms of the facility for such tasks. In situations where personnel require gowning and/or personnel protective equipment isolate themselves and/or protect their bodies from the environment of the facility, use of paper floorplan maps and the like marked with for example, sampling locations in facility room(s) and/or area(s), may not be possible due to the risk of contamination of cleanrooms and/or the impracticality and expense of sterilizing anything but essential tools and equipment to bring into cleanrooms.

Similarly, personnel performing air sampling and monitoring of areas and/or rooms in facilities may benefit from bringing with them to sampling locations various job aids such as instruction manuals, standard operating procedures, and the like, including in paper formats. Due to the contamination risk and unavailability and/or impossibility of sterilizing such items for use by workers in cleanrooms, the lack of ready information for use by personnel performing air sampling and monitoring may present difficulties or inefficiencies for such tasks.

Furthermore, workers may be required to perform air sampling and monitoring tasks in conjunction with recording additional information such as location(s) where samples are taken, observations made about, for example, the facility environment, and notes regarding operations, settings, and/or conditions of equipment and instrumentation being used like portable particle analysis devices. As with maps and job aids, including in paper formats, use of paper notepads and writing implements may not be feasible in particular area(s) and/or room(s) (e.g., cleanroom(s)) of a facility. It would be beneficial for personnel and other users engaged in facility air sampling, monitoring, and related tasks to be able to access the aforementioned information to assist their work in a manner that does not present contamination risks to cleanrooms and other sensitive and controlled facility areas and rooms. Embodiments of the disclosure enable integration of navigation maps and tools with obtaining and storing metadata like sampling locations, instrument sampling and/or analysis settings (e.g., "recipes") attached as metadata to, and stored in association with, the instrument data for the analysis of air samples. Other information (e.g., user identity) related to operation of portable particle sampling and/or analysis devices may also be useful and beneficial to attach as metadata to, and store in association with, the instrument data for analysis of air samples.

Example 3: Firmware Design for Multilevel Navigation Maps and Associated Particle Sample Data Management of Portable Particle Analysis Devices A person having ordinary skill in the art will appreciate that the below-described embodiments may be practiced in conjunction with not only the specific devices and systems described in Examples 3 and 4, but also those discussed with respect to Examples 1 and 2, along with any air sampling and/or analysis instrumentation for which the various technical, practical, and regulatory compliance benefits inuring from the embodiments disclosed herein may be realized in like manner. Thus, a further benefit of the disclosed embodiments is that they may be integrated, as by retrofitting and/or upgrading, into existing air sampling and monitoring equipment and/or instrumentation to provide like advantages in a variety of practical settings.

Embodiments of the disclosure, as in this Example 3, as well as Example 4, below, may employ a three-level map system displayed to users of portable air sampling and/or analysis equipment. The three-level map system consists of at least three spatial tiers or levels. The levels correspond to "Facility", "Area" and "Room". The top-most spatial tier is the facility, which may be a building. The middle tier(s) is/are area(s) of the facility. The lowest level tier is a room, which may include one or more rooms within a larger room. The three-level maps system may be made available on a display and/or touch-screen of a portable aerosol particle counter, for instance. Each map level may include one or more textual and/or graphical symbols on it to indicate selectable items including, for example and without limitation, pin(s). In one embodiment, the top-level map allows pins to be touched (selected) to select an Area within the facility, the second level map allows pins to be touched that correspond to one or more rooms within an area, and the lowest level map allows pins on the room map to be touched that correspond to a location for which air sampling and/or monitoring is to be performed. In an example, the name of selected area, room, and/or and sampling location is automatically appended as metadata to any samples taken and/or analytical data pertaining thereto (e.g., particle counts).

A recipe feature is also integrated with the maps. A room monitoring recipe or cleanroom certification recipe (e.g., statistics recipe) may be attached at a room level. A sampling recipe may be attached to the sampling location(s) that may be present and user-selectable at area and/or room level(s). In an embodiment, when a recipe is attached at the room level, for instance, selecting the room from an area level map causes a pop-up message to be generated and displayed to the user informing him or her that the recipe will be loaded. Similarly, when a recipe is attached at the location level, selecting the location may also causes the same or similar action to occur in the disclosed embodiments.

Map files are graphics images in standard format (such as JPG, PNG, and any other suitable image file type capable of being read from a memory device by a computing device (e.g., processor), and further capable of being adequately displayed to a user using an electronic display device). The map files are created external to the particle counter and stored in memory device(s) located in, on, and/or at some position remote from the portable particle sampler and/or analyzer. Processor(s) cause the map file being read from the memory device(s) to be displayed to user on the display device position in or on the portable particle sampler and/or analyzer in view of a user thereof. In an example, once downloaded to a portable particle counter, for instance, the map files are configured by tagging different points on the map with areas, rooms and locations as required. In another example, the map files are so configured prior to being downloaded to the particle counter. In yet another example, the map files are accessed remotely (e.g., via a wireless data communication protocol using transceivers) for display to users by one or more processor and/or computing device(s)

of the particle counter from a memory device located outside of the particle counter. The configured maps (and other instrument configuration settings, e.g., recipes) may, via wired and/or wireless data communication mechanisms and protocols, be exported and/or imported from one instrument to another to provide ease of use and operational efficiency.

The disclosed embodiments, described herein as non-limiting examples, further provide facilitation of users' navigation through and between the various spatial tiers of the facility. By providing a visual indication of both the physical layout (e.g., floorplan) and positions of sampling location(s) in the facility (e.g., in room(s) thereof), the disclosed embodiments, effectively reduce probabilities of human error of sampling location selections and related tasks during deployment of portable particle sampling and/or analysis devices. Through computationally-, memory-, and power-efficient user friendly integration of the interactive maps feature with sampling operations and sample data storage in association with unique identifiers like sampling location name, names of the respective spatial tier where samples were taken and/or analyzed, the recipe(s) used therefor, and additional useful information, the disclosed embodiments facilitate downstream data processing and report generation, thereby increasing the efficiency of these tasks. These, and other technical and practical advantages appreciable to persons of ordinary skill in the art, further facilitate users of the disclosed systems, methods, and software complying with standard operating procedures and/or regulatory requirements (e.g., United States Code of Federal Regulations, 21 C.F.R. Part 11 for FDA-regulated operations).

Figure 6:
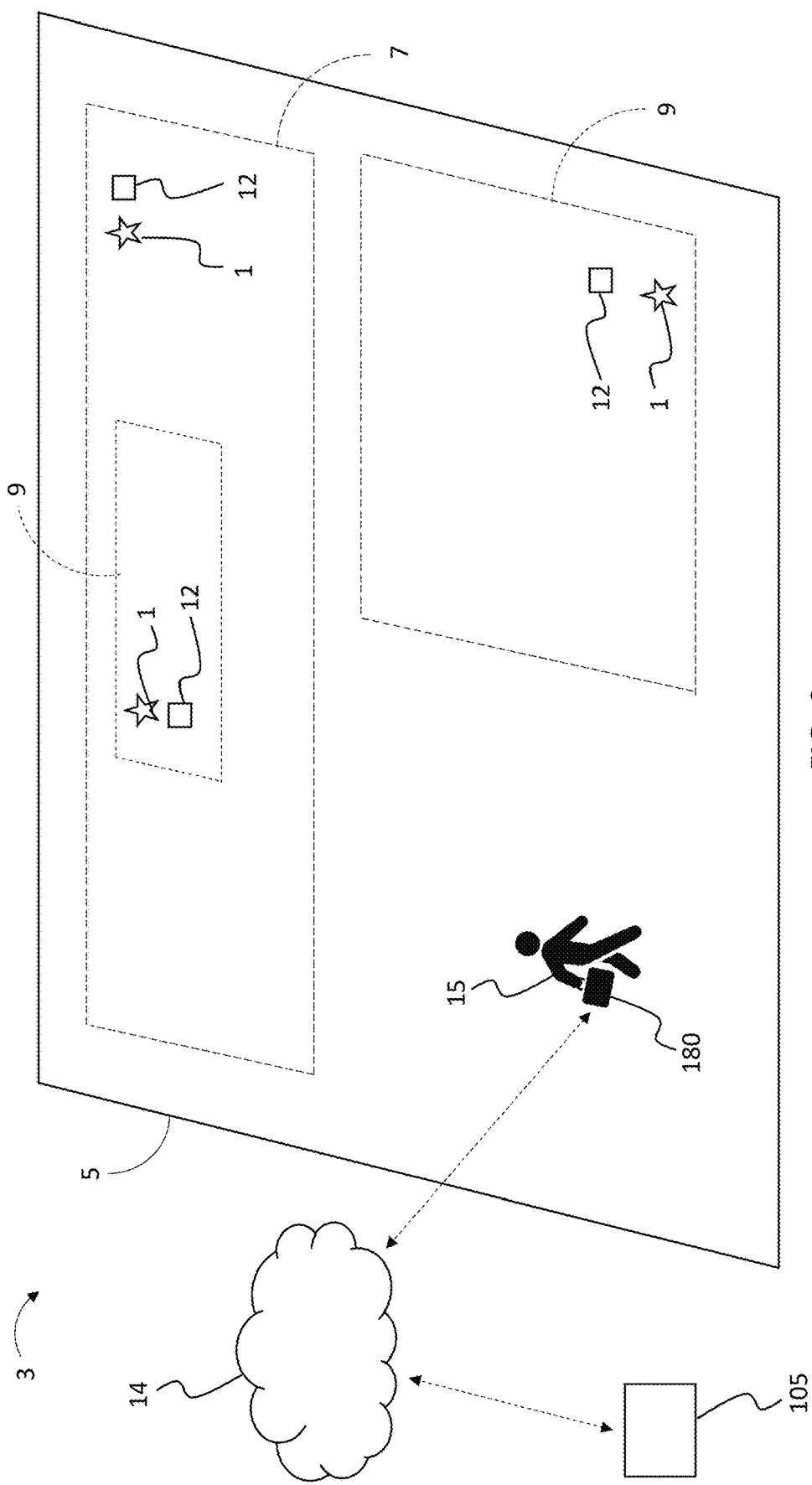
FIG. 6 illustrates a floor plan of a facility environment where a portable particle analysis device may be used.

FIG. 6 illustrates a floor plan of a facility 3 environment where a portable particle analysis device 180 may be used. Facility 3 may include a plurality of spatial tiers. The spatial tiers of the facility 3 are characterized from a high level perspective of the entire facility down to specific sub spaces of and/or inside facility 3. In an embodiment, the spatial tiers include: at least one building 5 (e.g., as the facility 3), at least one area 7, and at least one room 9. In FIG. 6, facility 3 is illustrated without walls, a roof, and similar structures solely for purposes of clarity, and not to imply that the disclosed embodiments are particularly suited to certain types of facilities; this is not the case.

A user 15 of the portable particle analysis device 180 may be tasked with sampling at least one sampling location 1 in the facility 3. For purposes of this disclosure, "sampling location(s) 1" is used synonymously with "sampling position(s)," as described above, including with reference to Examples 1 and 2. To do so, user 15 enters facility 3 and navigates throughout facility 3 to the sampling location(s) 1. While, for instance, walking through the facility 3, user 15 carries the portable particle analysis device 180 during the course of entering and exiting area(s) 7 and/or room(s) 9 to and/or from the sampling location(s) 1.

Figure 7:
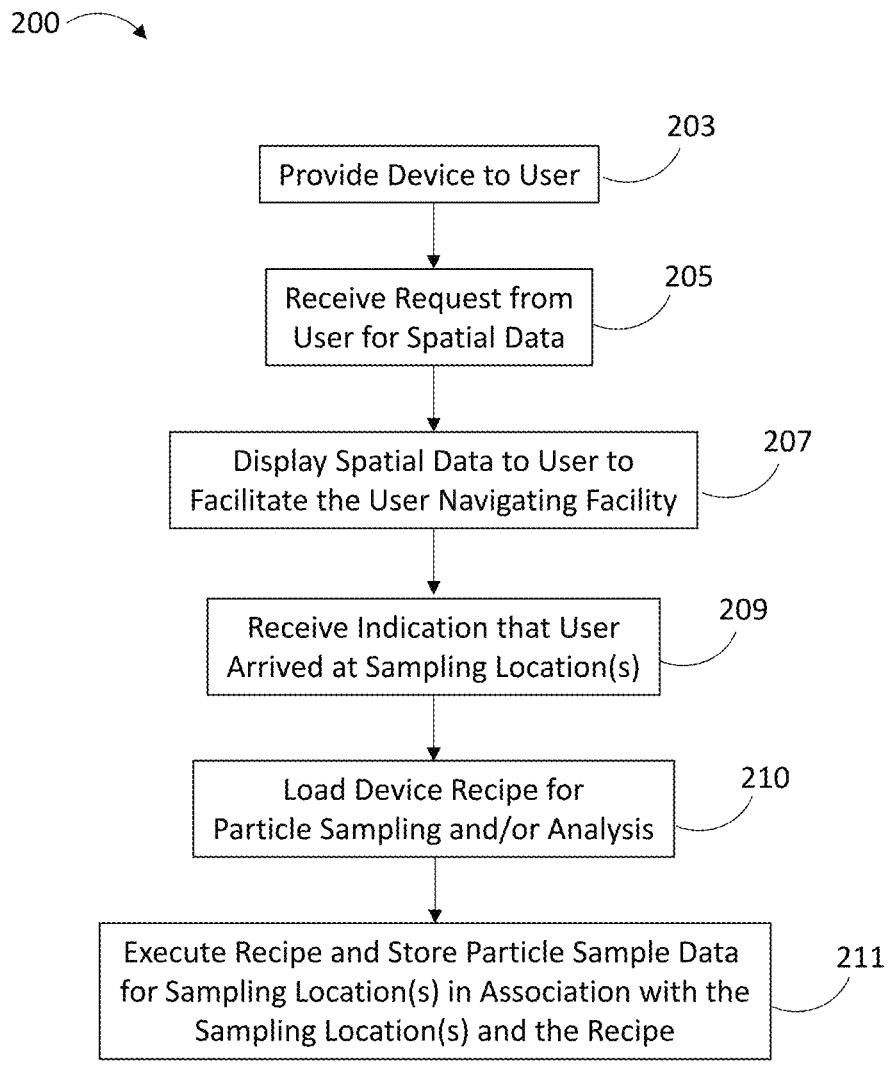
FIG. 7 illustrates a flow chart of a method of operating the portable particle analysis device shown in FIG. 6.

FIG. 7 illustrates a flow chart of a method of operating the portable particle analysis device shown in FIG. 6, in accordance with an embodiment. Although method 200 is described in the context of a computer-implemented method performed by one or more processors, the method 200 may also be performed by a program, custom circuitry, or by a combination of custom circuitry and a program. For example, the method 200 may be executed by a CPU (central processing unit), a GPU (graphics processing unit), or any processor, micro-controller, or application-specific integrated circuit (ASIC) capable of implementing, at least in part, the processes and steps described herein with respect to the various embodiments of method 200. For instance, method 200 may be implemented by portable particle analysis device 180 functioning as an embedded system. Furthermore, persons of ordinary skill in the art will understand that any system that performs method 200 is within the scope and spirit of embodiments of the present disclosure.

At step 203, the portable particle analysis device 180 (hereinafter referred to simply as "device 180") is provided to the user 15 tasked with sampling the sampling location(s) 1 in the facility 3 (e.g., in a cleanroom type of room 9 thereof). In an example, the user 15 carries device 180 through facility 3 using a handle, as shown in FIG. 6. In another example, not shown in FIG. 6, user 15 totes device 180 positioned on a cart or other wheeled device. In yet another example, also not shown in FIG. 6, user 15 carries device 180 as a backpack. In any event, device 180 is provided to user 15 at step 203 such that user 15 may safely and effectively transport device 180 through the facility 3 to the sampling location(s) 1 where the sampling task(s) are to be performed. For step 203, the device 180 may be provided to the user 15 either before or after user 15 enters facility 3, or specific area(s) 7 or room(s) 9 thereof.

At step 205, a processor of the device 180 receives a request from the user 15 for spatial data for one of the plurality of spatial tiers of the facility 3. The spatial data is stored in one or more memory devices (collectively referred to herein more simply as "memory") in communication with the device 180 processor. In an example, the user 15 requests the spatial data to facilitate his or her navigation through facility 3 to reach the sampling location(s) 1. In another example, the user 15 requests the spatial data to facilitate his or her arrival at the facility from a location remote from the facility (e.g., for a facility having a number of buildings positioned on a campus), either instead of, or in addition to, the user 15 requesting the spatial data to facilitate navigation through a building of the facility.

At step 207, the device 180 processor causes the spatial data to be displayed to the user 15 to facilitate the user 15 navigating to the at least one sampling location 1. The spatial data is displayed to the user 15 on a display positioned on or in device 180 and in view of the user 15. In one embodiment, the processor causes the spatial data to be displayed to the user 15 at step 207 in response to the request having been received by the device 180 processor at step 205.

At step 209, the processor of the device 180 receives an indication that the user 15 has arrived at the sampling location(s) 1 in the facility 3. In one embodiment, the user 15 interacts with device 180 processor using an input/output (I/O) device positioned on or in device 180. For example, and without limitation, the user 15 may press a button and/or operate a switch on device 180, speak into a microphone, perform tapping and/or other movements upon device 180, perform various touching actions and motions on a graphical user interface (GUI) (which the device 180 processor may also utilize to cause the spatial data to be displayed to the user 15), upon arriving at the sampling location(s) 1. The sampling location(s) 1 may be labeled (e.g., as text, numbers, and/or graphics provided in view of user 15 on a wall and/or floor of facility 3), such that the user 15 may navigate there, provide the indication for step 209, and performing the sampling task(s) using device 180. In the embodiment, such user 15 actions received by device 180 processor via I/O devices provide the aforementioned arrival indication for step 209.

In another embodiment, the device 180 processor receives the arrival indication at step 209 automatically and without direct user 15 interaction with device 100. In an example, facility 3 includes one or more RFID transmitters 12 positioned at or proximal the sampling location(s) 1, as shown in FIG. 6. In the example, device 180 includes one or more receivers for receiving signal(s) from the RFID transmitter(s) 12. Upon the user 15 successfully navigating to the sampling location(s) 1, the device 180 processor receives the arrival indication in response to the device 180 receiver receiving the signal from the RFID transmitter 12. Instead, or additionally, the device 180 processor causes a visual or audible notification to be provide to the user 15 in response to receiving the arrival notification according to this example. In another example, RFID transmitters 12 are employed for this Example 3 in like manner as described with reference to "tagging" and "RFID and corresponding reader" (e.g., receiver antenna(s) positioned on, in, or proximal device 180) in the "Summary" section of the disclosure.

In yet another embodiment, device 180 includes a barcode and/or QR code reader in communication with device 180 processor and/or memory. A QR code is technically a type of barcode. Traditional (one dimensional) barcodes are a pattern of stripes. Newer (two dimensional) barcodes are generally patterns within a square. There are multiple types of two dimensional barcodes such as QR, Aztec and Data Matrix. The device 180 may include a two dimensional barcode reader to support multiple formats of both one- and two dimensional barcodes. In an example, the sampling location(s) 1 of facility 3 may include may include bar and/or QR codes positioned at or proximal sampling location(s) 1 and in view of user 15. In a use case, upon the user 15 successfully navigating to the sampling location(s) 1, user 15 positions the barcode and/or QR code reader of device 180 to point toward the barcode and/or QR code label at or proximal the sampling location(s) 1. In this embodiment, the device 180 processor receives the arrival indication at step 209 in response to the device 180 barcode and/or QR code reader receiving the signal from the barcode and/or QR code reader of device 180.

At step 210, the device 180 processor loads a device 180 recipe from the memory. As used herein, "recipe" means parametric sampling information, or cleanroom certification parameters. Sampling information may include, but is not limited to, the number of samples, the time or volume to sample, alarm information, as well as which sampling location 1 within a room 9 to sample. Cleanroom certification parameters include the sampling parameters required for a specific room to meet a specific type and class of certification. Device 180 may implement several types of recipes for the sampling and/or analysis, as described herein. In an example, a basic sampling and/or analysis includes: a time for which device 180 will sample air of facility 3 at a respective sampling location 1, a volume of air to be sampled, which may include a flow rate, a number of samples to be taken, and alarm limits, which may be associated with a single sampling location 1 only. In another example, a certification recipe for sampling and/or analysis includes: at least of portion of those parameters describe above for the "basic" recipe, along with additional parameters for certifying an entire room 9 having one or more sampling location(s) 1 in it for purposes of standards and/or regulatory guidelines (e.g., ISO, FDA, EMEA, and/or cGMP). Thus, the "certification" recipe type applies to an entire room 9 to be certified. In yet another example, a monitoring recipe includes a superset of the "basic" recipe. Like the "certification" recipe, the monitoring recipe applies to rooms 9, and both require sampling at some specification set of sampling location 1 within a room 9. Using the "monitoring" recipe enables device 180 to execute one or more sampling and/or analysis recipe(s) at multiple sampling locations 1 in a given room 9. As such, the "monitoring" recipe is tied to the room 9, instead of being tied to the sampling location 1.

The recipe is loaded from memory at step 210 for and/or to facilitate the device 180 particle sampling and/or particle analysis, including with any necessary user 15 interaction and/or additional actions by the user 15 beyond the user 15 bringing the device 180 to the sampling location(s) 1. In one embodiment, the device 180 recipe is loaded from the memory at step 210 in response to the indication that the user 15 has arrived at the sampling location(s) 1 having been received by the device 180 processor at step 209. In an example, user 15 samples particles and/or performs additional or other tasks using the device 180 according to the recipe loaded from memory. At step 210, the same recipe may be loaded from memory for the sampling and/or other tasks to be performed and/or facilitated by user 15 using device 180 at the one or more sampling location(s) 1 in facility 3. Instead, or additionally, different recipes may be loaded from memory for the sampling and/or other tasks to be performed and/or facilitated by user 15 using device 180 for two or more of a plurality of sampling location(s) 1 in facility 3. For instance, a first sampling location 1 in a first room 9 may call for a first recipe to be loaded from memory at step 210, and a second sampling location 1 in a second room 9 may call for a second recipe to be loaded from memory at step 210.

At step 211, the processor of device 180 stores particle sample data for particles sampled and/or analyzed at the sampling location(s) 1 in the memory in association with unique identifiers. The unique identifiers may be stored in memory as metadata. Device 180 processor and/or additional and/or other processors may utilize these metadata contemporaneously and/or at some later time, as for example and without limitation, for report generation related to particle sampling and/or analysis. The unique identifiers for which the particle sample data for sampling location(s) 1 are stored in association with include the at least one sampling location 1 and/or the recipe(s) used by device 180. In one embodiment, the device 180 processor stores the particle sample data in association with the unique identifiers in response to the device 180 sampling and/or analyzing the particles at the sampling location(s) 1, where the device 180 performs the sampling and/or analyzing of the particles, at least in part, by executing the recipe(s) loaded from memory at step 210. In a use case, user 15 arrives at a sampling location 1 in facility with the device 180, the device 180 processor receives the arrival indication as described above with reference to step 209, the device 180 processor loads the recipe from memory, sampling and/or analysis of particles is caused to be performed by the device 180 processor and/or user 15 using device 180 according to the loaded recipe(s) at the sampling location 1, and upon the sampling and/or analysis being at least partially completed, device 180 processor responsively stores the particle sample data at step 211 in the memory in association with the unique identifiers including the respective sampling location 1 and the recipe(s) loaded for use by device 180 at the respective sampling location(s) 1.

More illustrative information will now be set forth regarding further details of various algorithms, architectures, and features with which the foregoing framework may be implemented in performance of method 200, per the desires of the user 15. It should be strongly noted that the following information is set forth for illustrative purposes and should not be construed as limiting in any manner. Any of the following features may be optionally incorporated with or without the exclusion of other features described.

Figure 8:
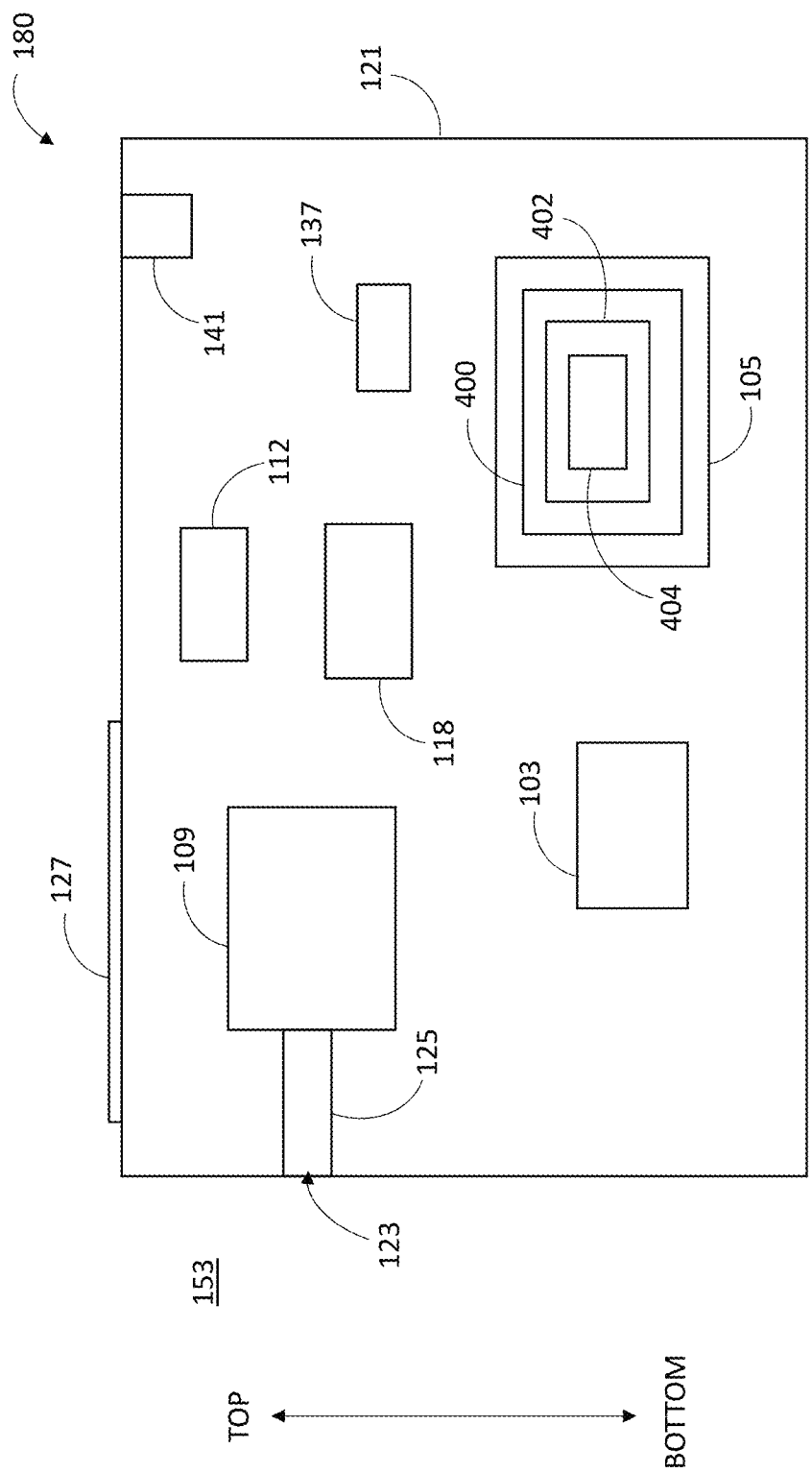
FIG. 8 illustrates features of the portable particle analysis device shown in FIG. 6 that may be used with the method of FIG. 7, according to an embodiment of the disclosure.

FIG. 8 illustrates features of the portable particle analysis device 180 shown in FIG. 6 that may be used with the method 200 of FIG. 7, according to an embodiment of the disclosure. Device 180 includes a device housing 121. A carrying handle may be coupled to the housing 121 or otherwise be positioned through and/or on housing 121 to facilitate user 15 carrying device 180. The device housing 121 includes a sampling port 123. The device 180 includes a particle sampler 125 positioned in the housing 121 and in flow communication with the sampling port 123. The device 180 includes a sample analyzer 109, and a display 127 visible to the user 15 of the device 180.

The device 180 includes one or more processors 103 (collectively referred to herein simply as "processor 103") in communication with: the display 127, the sample analyzer 109, at least one memory device 105 (collectively referred to herein simply as "memory 105"). In one embodiment, memory 105 is positioned in or on device housing 121. Instead, or additionally, in another embodiment, memory 105 is positioned outside of and/or remote from device housing 121. In such other embodiments, processor 103 and memory 105 are in communication with one another via, and communicate with one another using signals (e.g., encoded data signals) sent and/or received through, a network 14, as shown in FIG. 6. In an example, communication among and between processor 103 and remote memory 105 using network 14 includes wireless communication equipment and protocols. Wireless communication among and between device 180 processor 103 and remote memory 105 is facilitated by transceivers positioned in or on device 180 (e.g., transceiver 137) and/or elsewhere in facility 3 (e.g., WiFi routers and/or modems) (not shown in FIG. 6). In another example, communication using network 14 includes wired communication equipment and protocols. In yet another example, network 14 communication includes a combination of wireless and wired communication equipment and protocols. In an example, communication among and between device 180 processor and remote memory 105 includes wireless and/or wired communication equipment and protocols for utilizing cloud-based processing, storage, and/or communication resources. In an example, network 14 communication utilizes the Internet, including, without limitation, Internet of Things (IoT) protocols, practices, and/or standards.

In an example, memory 105 is or includes a non-transitory computer-readable medium 400. Non-transitory computer-readable medium 400 stores as software 402 processor-executable instructions for operating the portable particle analysis device 180 in accordance with, for example, the disclosed embodiments of method 200. In an example, processor-executable instructions stored as software 402 includes one or more software modules 404. When executed by processor(s) 103 that are in communication with memory 105, the processor-executable instructions cause the processor(s) 103 to implement and/or otherwise perform, at least in part, one or more of the disclosed operations, steps, and/or processes of method 200, as described herein. "Software" (e.g., software 402) is used synonymously with "firmware" throughout the entire disclosure.

In one embodiment, step 205 of method 200 is performed and/or otherwise facilitated, at least in part, by processor 103 executing software instructions stored in a spatial data request receiving module 404. In another embodiment, step 207 of method 200 is performed and/or otherwise facilitated, at least in part, by processor 103 executing software instructions stored in a spatial data displaying module 404. In yet another embodiment, step 209 of method 200 is performed and/or otherwise facilitated, at least in part, by processor 103 executing software instructions stored in an arrival indication receiving module 404. In still another embodiment, step 210 of method 200 is performed and/or otherwise facilitated, at least in part, by processor 103 executing software instructions stored in a device recipe loading module 404. In another embodiment, step 211 of method 200 is performed and/or otherwise facilitated, at least in part, by processor 103 executing software instructions stored in a sample data storing module 404. As will be appreciated by persons of ordinary skill in the art, the various modules 400 described above may share particular functional blocks, or they have unique blocks not share by other modules 404. Likewise, software instructions stored in memory 105 as module(s) 404 may be organized in a distributed, centralized, or both, architecture, and device 180 may include additional or other hardware and software components to facilitate troubleshooting, cybersecurity, operational auditing, and/or periodic updates to software 402.

Device 180 may include at least one I/O device 112 positioned on or in device 180. Among several possible uses for I/O device(s) 112—e.g., to control a brightness, contrast, etc. of display 127, and/or to power device 180 on and off, or place processor 103 in a low power or sleep mode state—I/O device 112 may facilitate user 15 providing and/or initiating actions and inputs for processor 103 to receive, at step 209, the indication that the user 15 has arrived at the sampling location(s) 1 in the facility 3 (also referred to herein more succinctly as the "arrival indication").

Device 180 may include at least one receiver 118 positioned in or on device 180. Among several possible uses for receiver(s) 118—e.g., to facilitate the loading of the recipe from a remote memory 105 for step 210—receiver 118 facilitates processor 103 receiving signal(s) from RFID transmitter(s) 12 in facility 3 to automatically provide processor 103 the arrival indication at step 209.

Device 180 may include at least one barcode and/or QR code reader 141 positioned in or on device 180 and in view of at least a portion of the device 180 exterior space 153. Among several possible uses for reader(s) 141—e.g., to facilitate decoding of information displayed at one or more locations in facility 3 in the form of barcodes and/or QR codes for storing in memory 105 and/or displaying on the display 127 of device 180—reader 141 facilitates user 15 scanning the bar- and/or QR codes to facilitate providing processor 103 the arrival indication at step 209.

In operation of device 180, the processor 103 loads the recipe from memory 105 at step 210 and the particle sampling and/or particle analysis performed by device 180 and/or user 15 proceeds according to the recipe loaded. The air or other medium occupying the space 153 proximal the sampling port 123 of device is drawn in to the particle sampler 125 (e.g., by suction, vacuum, or like mechanisms). A flow path of the air or other medium into the particle sampler 125 portion of device 180 is directed toward the sample analyzer 109 portion of device 180. Instrumentation components in the sample analyzer 109 facilitate various qualitative and/or quantitative analyses of the sampled air or other medium including, for example and without limitation, particle counts and characterization of particle sizes. Such components of device 180 and further details and examples of the analyses that may be performed thereby are described with reference to optical particle counters, for example, in U.S. Pat. Nos. 7,745,469, 7,916,29, and 8,154,724, which are each incorporated by reference in their entireties to the extent they are not inconsistent with the present disclosure. In an example, the analyses performed by the sample analyzer 109 of device 180 result in the sample data pertaining to characterization(s) of the sampled particles and which is/are stored by processor 103 in memory 105 in association with the sample location(s) 1 and/or unique identifier(s) at step 211.

Figure 9:
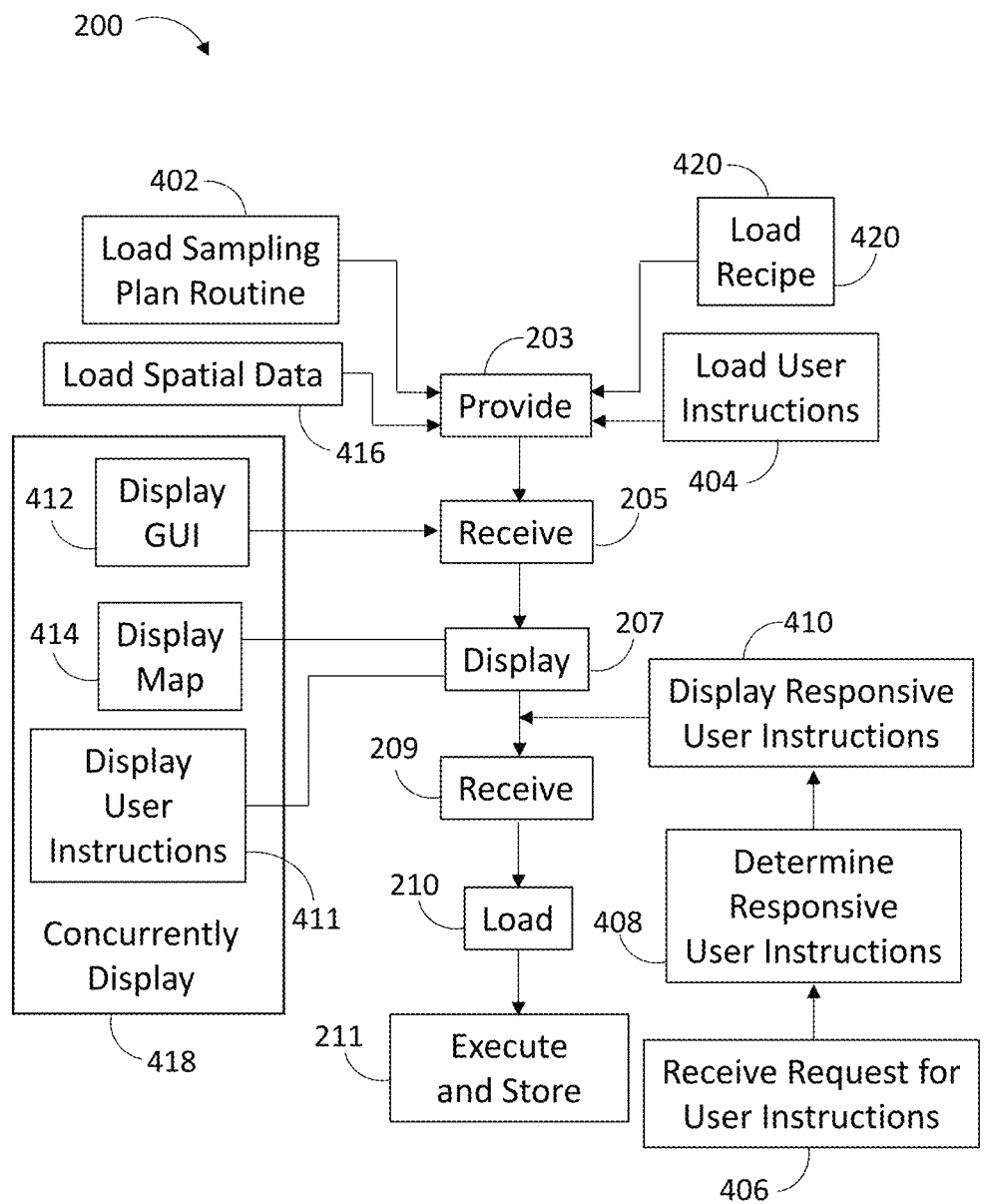
FIG. 9 illustrates aspects of the method of FIG. 7, according to some embodiments of the disclosure.
Figure 10:
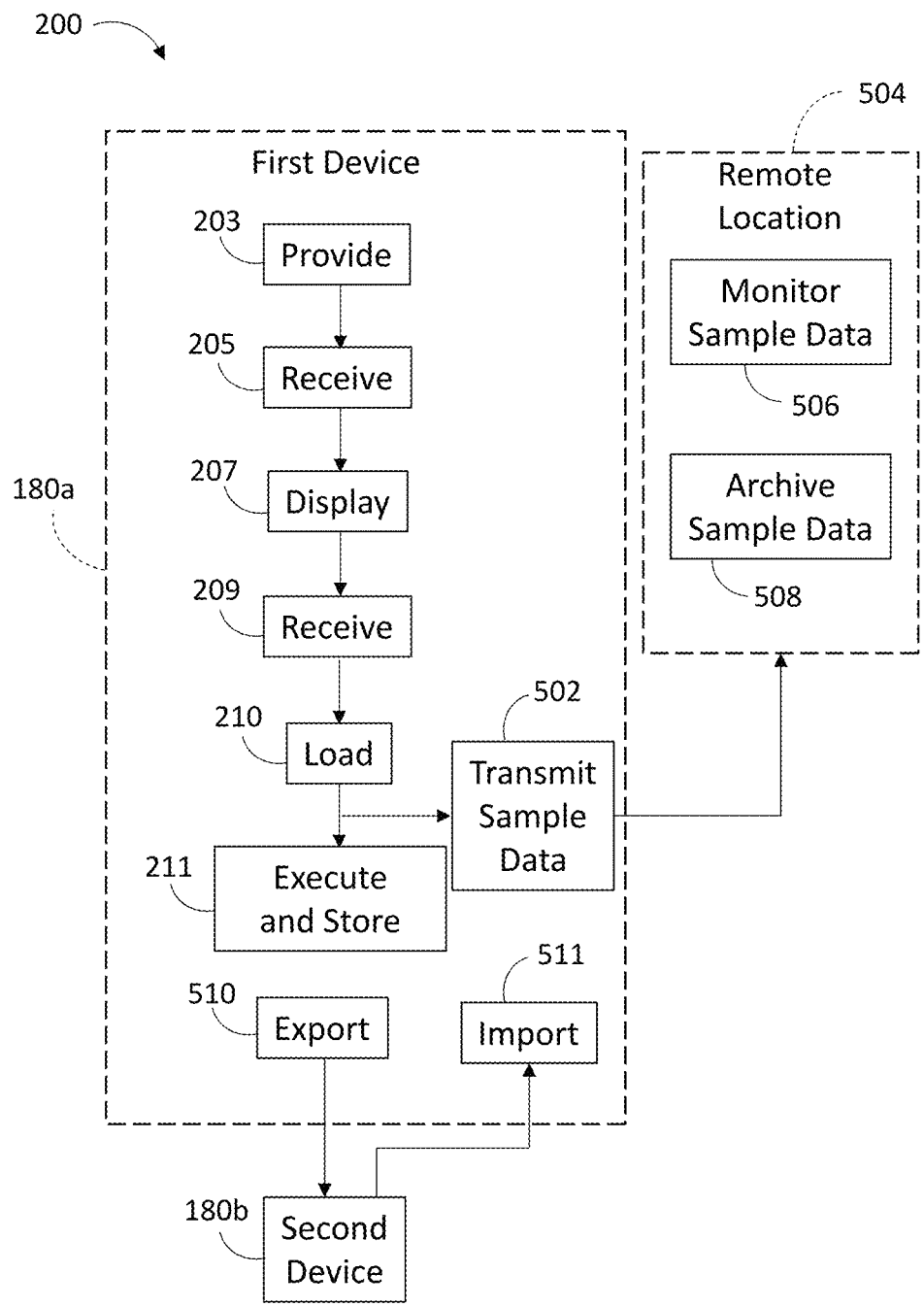
FIG. 10 illustrates additional aspects of the method of FIG. 7, according to some embodiments of the disclosure.

FIGS. 9 and 10 illustrate aspects of the method 200 of FIG. 7, according to some embodiments of the disclosure. The following description of FIGS. 9 and 10 is organized according to the aforementioned steps of method 200 and, as such, reference to FIGS. 6-8 and the features shown and/or numbered therein, and described above, is made throughout. It should be strongly noted that the following information is set forth for illustrative purposes and should not be construed as limiting in any manner. Any of the following features may be optionally incorporated with or without the exclusion of other features described.

Step 203: Providing the device 180 to the user 15.

Referring to FIG. 9, in an embodiment, method 200 includes a step 402 by which a sampling plan routine is loaded by the processor 103 to and/or from memory 105. In an example, the sampling plan routine loaded at step 402 corresponds to the sampling of the facility 3 by the user 15. For instance, the sampling plan routine may include text and/or graphics which the processor 103 causes to be displayed on the device 180 display 127 and which provide information to user 15 such as an order of room(s) 9, area(s) 7, and/or sampling location(s) 1 for user to navigate to with device 180 for performing the sampling and/or other tasks at the sampling location(s) 1. In an example, the device 108 is provided to the user 15 at step 203 with the sampling plan routine pre-loaded in memory 105. In an embodiment, the sampling plan routine loaded by processor 103 to and/or from memory 105 at step 402 includes the spatial data of facility 3 requested by user 15 and caused to be displayed by processor 103 on display 127 at step 205 and step 207, respectively.

In an embodiment, method 200 includes a step 404 by which user instructions are loaded by processor 103 to and/or from memory 105. In an example, the user instructions correspond to the sampling plan routine loaded to and/or from memory 105 at step 402. For instance, the sampling plan routine may include text and/or graphics which the processor 103 causes to be displayed on the device 180 display 127 and which provide information to user 15 such as how to operate device 180 and/or I/O device(s) 112 thereof, how to troubleshoot device 180, how to charge a rechargeable battery power supply of device 180, and other or additional useful information to maximize a probability of user 15 success with performing the sampling of the sampling location(s) 1 in facility 3.

In an embodiment, method 200 includes a step 406 by which processor 103 receives a request from user 15 for the user instructions. Where a plurality of versions and/or types of content for user instructions are loaded at step 404, this user 15 request received at step 406 may include an indication of which of a plurality of user instructions is desired to be displayed on display 127 for viewing by user 15.

In one embodiment, method 200 includes a step 408 by which the processor 103 determines responsive user instructions for the at least one sampling location 1. In an example, the processor 103 receives, at step 209, the arrival indication and causes corresponding user instructions to be displayed to user 15 on display 127 for the respective sampling location 1. In another example, the arrival indication received by processor 103 at step 209 from the user 15 includes an indication of the particular sampling location 1 and processor determines, at step 408 the appropriate user instructions to display to user 15 via display 127. In the embodiment, method 200 includes a step 410 by which the responsive user instructions determined at step 408 are caused to be displayed by processor 103 on the display 127 to user 15. The responsive user instructions displayed to user 15 via display 127 may be so displayed at step 410 as text, graphics, and/or combinations thereof.

Step 205: Receiving user 15 request for spatial data of the facility 3.

Referring to FIG. 9, in an embodiment, method 200 includes a step 412 by which processor 103 causes a graphical user interface (GUI) to be displayed on the display 127 of device 180. In an example, display 127 is a touch-screen-type display 127, and display 127 is thus an I/O device 112 of device 180. In the example, the user 15 interacts with the GUI via the touchscreen of the display 127. Instead, or additionally, display 127 is a mouse/cursor-type display 127, and display 127 and a mouse and/or mouse pad coupled to processor 103 and/or to display 127 are thus I/O devices 112 of device 180. In that case, example, the user 15 interacts with the GUI via the mouse and cursor for the display 127. The GUI which is caused to be displayed by processor 103 on display 127 at step 412 is configured and/or adapted for facilitating user 15 interacting with processor 103 and/or memory 105 for purposes of operating device 180, including directing, as needed, the functionality of components of device 180 including, without limitation, particle sampler 125 and/or sample analyzer 109.

In an embodiment, at step 205, the processor 103 receives the request for the spatial data of facility 3 from user 15 via the GUI. In the embodiment, the request for spatial data received by processor 103 from user 15 via the GUI at step 205 is so received via a drop down menu of the GUI. In an example, the drop down menu includes textual and/or graphical indicators and/or descriptors of at least a subset of the plurality of spatial tiers of the facility 3. In that case, step 205 includes receiving, by the processor 103, an indication of which of the textual and/or graphical descriptors and/or indicators was touched by the user 15 on the drop-down menu.

Step 207: Displaying the spatial data to user 15.

Referring to FIG. 9, in an embodiment, in the use case in which step 205 includes the processor 103 receiving the indication of which of the textual and/or graphical descriptors and/or indicators was touched by user 15 on, for example, the drop-down menu of the GUI, the processor 103 causes the responsive spatial data to be displayed on display 127 at step 207 based on the indication of which of the textual and/or graphical descriptors were received by processor 103.

In an embodiment, at step 207, the processor 103 displaying the spatial data to the user 15 includes a step 414 of causing, by the processor 103, the responsive spatial data to be displayed as a graphical map on the device 180 display 127. In an example, the graphical map is stored in, and caused to be displayed to user 15 on display 127 by processor 103 from, memory 105 as one or more standard format image file(s). In an example, the standard format image file may be stored in memory 105 as a jpg file. In another example, the standard format image file may be stored in memory 105 as a png file. In yet another example, the standard format image file may be stored in memory 105 as a jpg file for one or more of a plurality of image files for graphical map(s), and also stored in memory 105 as a png file for one or more of a plurality of additional image files for additional graphical map(s) stored in memory 105.

In an embodiment, the graphical map stored in memory 105 and caused to be displayed on display 127 by processor 103 includes the at least one sampling location 1 of facility 3. In an example, the processor 103 causes the responsive spatial data to be displayed as a graphical map of the room 9 to the user 15, with the graphical map including the sampling location(s) 1 of the respective room 9. In one embodiment, method 200 includes a step 418 by which processor 103 causes the graphical map to be displayed to user 15 as a portion of the GUI. In an example, the processor 103 causes the GUI and the graphical map to be displayed to user 15 concurrently on the display 127.

In an embodiment, processor 103 causes responsive spatial data to be displayed on display 127 as graphical maps of user 15-selected spatial tiers. So, for example, a facility map shows areas, but not room(s) 9 and/or sampling location(s) 1. In the example, an area map shows room(s) 9, but not other area(s) 7 and/or sampling location(s) 1, while a room map shows sampling location(s) 1, but not other area(s) 7 and/or other room(s) 9.

In an embodiment, method 200 includes a step 416 by which processor 103 loads the spatial data to and/or from memory 105. The spatial data corresponds to at least a subset of the plurality of spatial tiers of the facility 3. In an example, the device 180 is provided to the user 15 at step 203 pre-loaded with the spatial data stored in, and accessible by processor 103, from memory 105. In an example, the spatial data includes one or more graphical maps for one or more of the plurality of spatial tiers of the facility 3. In the example, the step 207 of causing, by processor 103, the one or more graphical maps to be displayed to user 15 includes displaying the graphical map(s) to the user 15. In this case, the graphical map(s) displayed to user 15 on display 127 include textual labels and/or graphical labels for at least a subset of the plurality of spatial tiers of the facility 3. In one embodiment, step 418 of method 200 includes causing, by processor 103, the GUI and the graphical map(s) to be displayed to user 15 as a portion of the GUI. In an example, the processor 103 causes the GUI and the graphical map(s) to be displayed to user 15 concurrently on the display 127. In another embodiment, step 418 of method 200 includes causing, by processor 103, at least one of: the graphical map and the user instructions, to be displayed to user 15 as a portion of the GUI on the display 127.

Step 209: Receiving an indication that user 15 arrived at sampling location(s) 1.

Referring to FIG. 9, in an embodiment, step 412 of method 200 includes causing, by processor 103, the GUI to be displayed on the display 127. In the embodiment, the arrival indication at step 209 is received from user 15 via the GUI. In another embodiment, the arrival indication at step 209 is received by processor 103 through an automated process including, for example and without limitation, device 180 being positioned with a predetermined distance of sampling location 1 as, for instance, detected using location sensing and/or triangulation of signal transmitted by RFID transmitter(s) 12 and related means, as described herein.

Step 210: Loading the device recipe for particle sampling and/or particle analysis from memory 103.

Referring to FIG. 9, in an embodiment, step 210 includes loading the device 180 recipe according to the at least one sampling location 1 corresponding to the indication received by the processor 103 at step 209. In an example, the device 180 is provided to the user 15 at step 203 pre-loaded with at least one recipe stored in, and accessible by processor 103, from memory 105 for at least a subset of the facility 3 sampling location(s) 1.

Step 211: Storing particle sample data for sampling location(s) 1 in memory 105 in association with the sampling location(s) 1 and/or unique identifiers.

Referring still to FIG. 9, in an embodiment, step 211 includes storing the particle sample data in memory 105 in association with an identifier of the one of the plurality of spatial tiers containing the sampling location(s) 1 (e.g., a name of the room 9 containing the sampling location(s) 1). In another embodiment, step 211 includes storing in memory 105 the particle sample data in memory 105 in association with an identifier of the user 15 operating device 180 for purposes of the particle sampling and/or analysis at the sampling location(s) 1. In yet another embodiment, step 211 includes storing the particle sample data in memory 105 in association with a time and date at which the user 15 performed the sampling and/or analysis at the at least one sampling location 1 with the device 180.

Referring now to FIG. 10, method 200 includes a step 502 by which processor 103 transmits (e.g., via transceiver 137 and/or using a wired line connection) the particle sample data to a location 504 remote from device 180 and/or remote from facility 3. In one embodiment, step 502 facilitates implementation of a monitoring step 506 in method 200. In a use case, user 15 may position device 180 in one sampling location 1 in one room 9 of a facility 3 and leave it there for a predetermined amount of time for device 180 to sampling and/or analyze air proximal the particular sampling location 1. In an example, device 180 periodically transmits sample data and/or other useful and pertinent information to a remote location for storage and monitoring purposes. In such cases, user 15 is freed up to perform other useful tasks in facility 3, such as being provided with another device 180 to performing sampling and/or analysis in a second room 9 of the facility 3, according to the various embodiments and examples disclosed herein.

In another embodiment, step 502 facilitates implementation of an archiving step 508 in method 200. Thus, for example, sample data and/or other useful and pertinent information obtained and stored according to the present disclosure may be backed up so that if device 180 were to malfunction, the data would not be lost. In yet another embodiment, step 502 facilitates implementation of both the monitoring 506 and archiving 508 steps in method 200.

Still referring to FIG. 10, in an embodiment, the device 180 includes a first device 180a and at least a second device 180b. In the embodiment, method 200 may further include a step 510 by which at least one of: the spatial data of the facility 3, the device 180 recipe for the sampling and/or analysis, and an identifier of the user 15, is exported 510 from the first 180a to the at least a second device 180b, or vice versa. In an embodiment, method 200 may include a step 511 by which at least one of: the spatial data of the facility 3, the device 180 recipe for the sampling and/or analysis, and an identifier of the user 15, is imported 511 from the at least a second device 180b to the first device 180a, or vice versa.

Example 4: Graphical User Interface Embodiments

FIGS. 11A-11D illustrate screens of a graphical user interface (GUI) 1100 presented to users 15 of device 180 via display 127, according to some embodiments of the disclosure. The map feature of device 180 described above with reference to Example 3 provides support for the following map types: facility maps, area maps, and room maps. At least one Facility map is available with the map feature of device 180. It shows and allows selections of Areas 7 within a facility 3.

Figure 11A:
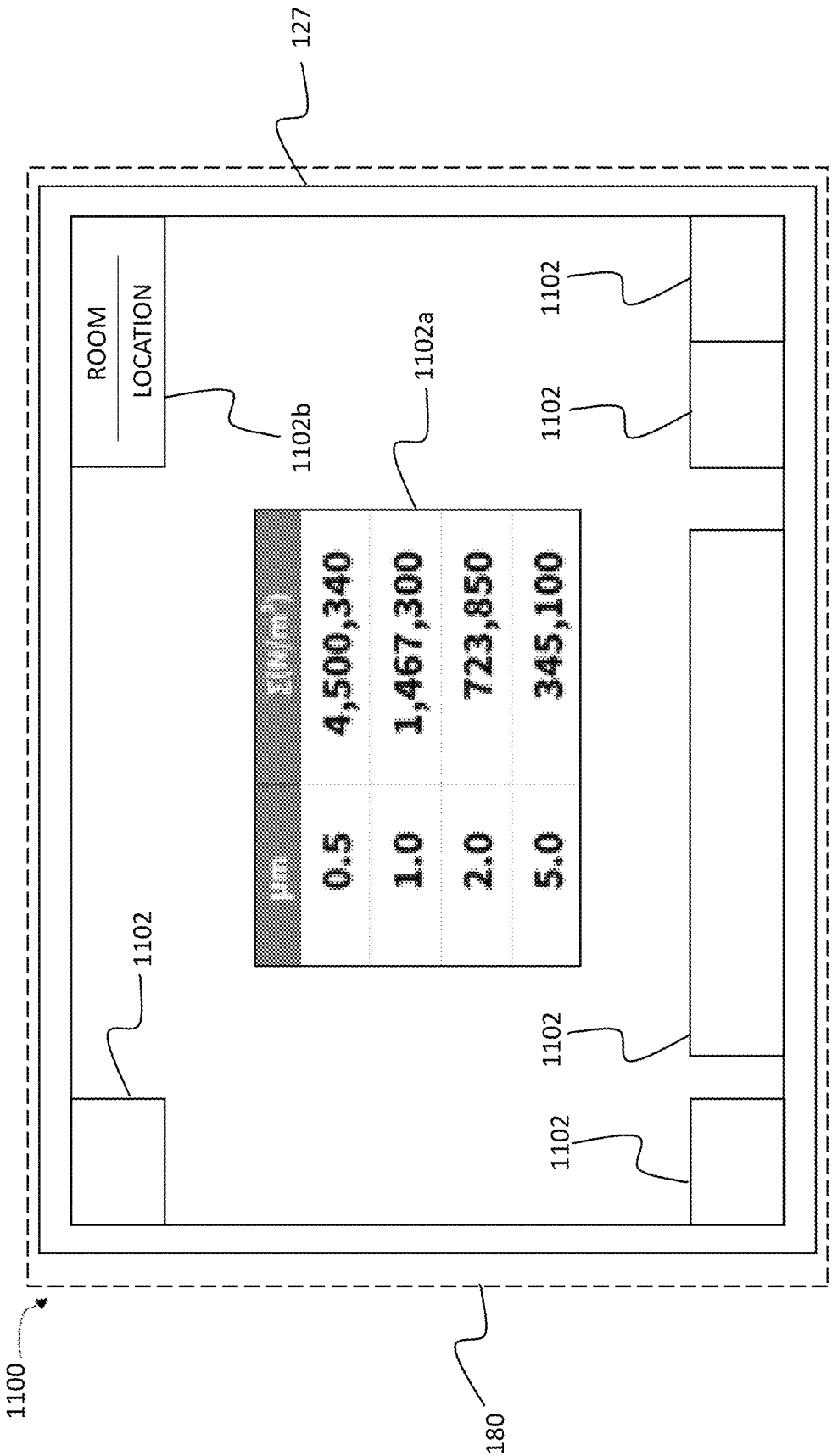

In FIG. 11A, a main screen of GUI 1100 including graphics 1102 is shown. Graphics 1102 may be touched or otherwise interacted with by user 15 to effect changes in what is currently being displayed to user 15 via GUI 1100. In an embodiment, the processor 103 causes a sample information graphic 1102a to be displayed to user 15 via the GUI 1100. Graphic 1102a may include sample data and unique identifier(s) for one or more particle samples analyzed by device 180 from sample(s) recently taken (e.g., for a predetermined number of samples and/or from a predetermined historical time period). In one embodiment, a graphic 1102b, when touched or otherwise interacted with by user 15, opens a drop down list from which user 15 may select maps to be displayed for facility 3 spatial tier(s), as desired. In an example, user 15 may select a map of facility 3 to be displayed from the drop down list from graphic 1102b. The facility map shows area(s) 7 of facility 3. In another example, from the drop down list, user 15 may select a map of a particular area 7 from the drop down list of graphic 1102b and/or from by touching or otherwise interacting with the area 7 as shown in the facility map being displayed to him or her on display 127. In yet another example, from the drop down list, user 15 may select a map of a particular room 9 to be displayed from the drop down list from graphic 1102b and/or by touching or otherwise interacting with the room 9 as shown in the area map being displayed to him or her on display 127. In one embodiment, from the room map 9 and/or from the drop list of graphic 1102b, the user 15 may also view the sampling location(s) 1 of the particular room 9 being displayed to him or her on display 127. Additionally, or instead, the sampling location(s) 1 shown on respective room maps may be touched or otherwise interacted with by user 15.

In an example, not shown in FIG. 11A, an as-displayed facility map 1101 on GUI 1100 shows the locations of the area(s) 7 (e.g., a first area and a second area adjacent to the first area) and/or room(s) 9 (e.g., five rooms 9) of the facility 3. In an embodiment, not shown in FIG. 11A, the facility map includes textual and/or graphical identifiers inside and/or proximal to the area(s) 7 and/or room(s) 9 displayed to user 15 as, for example, a floorplan on facility map. In the disclosed embodiments, the facility, area, and/or map(s) which processor 103 causes to be displayed on GUI 1100 in response to user 15 interactions therewith as described herein thus facilitates the user 15 navigating through facility 3 to sampling location(s) 1.

In an example, user 15 touching a portion the currently displayed map and/or a portion of drop down list of graphics 1102b enables user 15 to navigate to other (e.g., zoomed-in for additional detail) maps for area(s) 7 and/or room(s) 9 of facility. In another example, user 15 touching a portion of graphics 1102b causes processor 103 to display a drop down box to user 15 on the GUI 1100. For instance, in an embodiment, a user 15 touches the portion of graphics 1102b displaying the word "room", which, via processor 103, causes the GUI 1100 to display a drop down listing of the five rooms 9 of facility 3. With the drop down list of rooms 9 so-displayed on GUI 1100, user 15 touching the textual and/or graphical indicator displayed on the drop down list for one of the rooms 9 causes processor 103 processor 103 to display a detailed map on display 127 for that room 9. Similarly, user 15 may zoom to more detailed views of any of the areas 7 by touching that portion of graphics 1102b and proceeding to interact with GUI 1100 in like manner as described above for rooms 9. Likewise, user 15 may zoom to more detailed views of displaying the sampling location(s) 1 within particular rooms 9 by touching that portion of graphics 1102b and proceeding to interact with GUI 1100 in like manner as described above for rooms 9 and areas 7.

FIG. 11B illustrates examples of the aforementioned drop-down lists for areas 7, rooms 9, and sampling locations 1, which processor 103 may cause, in response to user 15 interaction with the GUI 1100, to display on the display 127 of device 180 to facilitate user 15's navigation to the sampling locations 1 for performance of tasks employing device 180. In the example illustrated in FIG. 11B, the listing of areas 7, rooms 9, and sampling locations 1 is a drop down list 1103 which the user 15 may interact with directly via touching display 127 at appropriate locations on the GUI 1100 and/or using another I/O device 112 (e.g., mouse/cursor-clicking interaction) with display 127.

FIG. 11B depicts two drop down lists 1103. A first drop down list 1103a lists the room(s) 9 present within particular area(s) 7 of facility 3, and a second drop down list 1103b lists the sampling location(s) 1 present within particular room(s) 9. In an embodiment, the drop down list(s) 1103 of areas 7, rooms 9, and/or sampling locations 1 in facility 3 may occupy the entirety, or a majority, of display 127. In such embodiments, GUI 1100 may include graphics displayed on GUI 1100 as a touch button 1104 that may be touched or otherwise interacted with by user 15 to cause, via processor 103, alternately expanding and contracting the size of drop-down list 1103 to occupy greater and lesser areas of display 127, respectively. When the drop-down list 1103 is in the contracted state, user 15 may interact with other portions of GUI 1100, as desired.

As shown in FIG. 11B, the drop down list(s) 1103 include accompanying graphics displayed on the GUI 1100 in the form of attached buttons. In an embodiment, the first drop down list 1103a includes a first spatial tier button 1105. User 15 touching button 1105 causes, via processor 103, GUI 1100 to display the second drop down listing 1103b. In the embodiment, the second drop down listing 1103b is not displayed on GUI 1100 unless user 15 touches or otherwise interacts with the first spatial tier button 1105. In an embodiment, the second drop down list 1103b includes a second spatial tier button 1107. With second drop down listing 1103b displayed on GUI 1100, user 15 touching button 1107 causes, via processor 103, GUI 1100 to stop displaying the second drop down listing 1103b, and display only first drop down listing 1103a on GUI 1100. In the example shown in FIG. 11B, the first drop down listing 1103a continues to be displayed on GUI 1100 after user 15 touching first button 1105 causes, via processor 103, GUI 1100 to display second drop down listing 1103b. In another example, not shown in FIG. 11B, user 15 touching first button 1105 causes, via processor 103, second drop down listing 1103b to be displayed on GUI 1100 and also causes GUI 1100 to stop displaying first down listing 1103a on GUI 1100.

Still referring to FIG. 11B, in an embodiment, the second drop down list 1103b includes a map button 1109. User 15 touching button 1109 causes, via processor 103, GUI 1100 to display the map corresponding to the room 9 selected (e.g., highlighted) by the user 15 on the second drop down listing 1103b on or at a portion thereof displaying a textual and/or graphical indicator for the respective room 9. In a use case, the user 15 has utilized the maps feature of device 180 to navigate to an area 7 (e.g., denoted as "AREA 1" in FIG. 11B) in facility 3, and then to a room 9 (e.g., denoted "ROOM 1" in FIG. 11B) in the area 7. Upon entering ROOM 1, the user 15 touches first spatial tier button 1105 on GUI 1100 to display the second drop down listing 1103b. User 15 desires to navigate with device 180 to one of the sampling locations 1 (e.g., denoted "LOC 1" in FIG. 11B) in ROOM 1, and so touches the portion of the second drop down listing 1103b having the textual and/or graphical indicator for LOC 1 in ROOM 1. In one embodiment, this action of the user 15 causes, via processor 103, the GUI 1100 to highlight that portion of second drop down listing 1103 on GUI 1100 corresponding to LOC1. The user 15 then touches the map button 1109, which causes, via processor 103, the room map for ROOM 1 to be displayed on GUI 1100 and, optionally, causes the second drop down listing 1103b to stop being displayed on the GUI 1100. In another embodiment, the user 15 touching the portion of the second drop down listing 1103b having the textual and/or graphical indicator for LOC 1 in ROOM 1 causes the GUI 1100 to immediately display the room map for ROOM 1. For either scenario in this use case, the GUI 1100-displayed room map for ROOM 1 may have the map position for LOC 1 and, optionally, for all other sampling location(s) 1 in ROOM 1, displayed using textual and/or graphical indicators, which facilitates user 15 navigating thereto.

Facility Maps, Area Maps, and Room Maps—

Figure 11E:
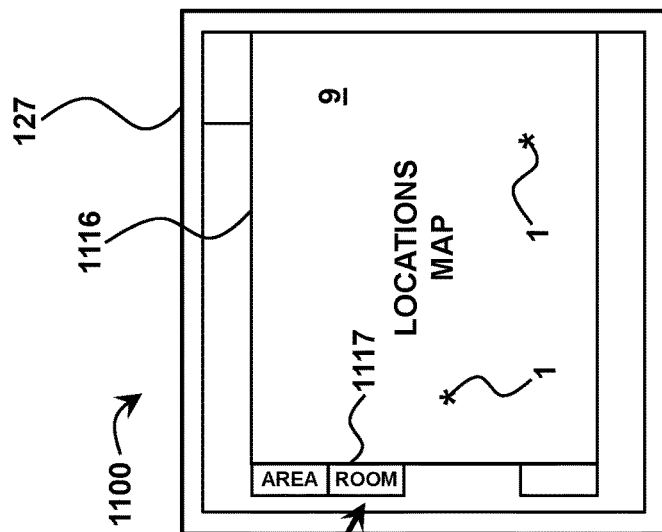
Figure 11D:
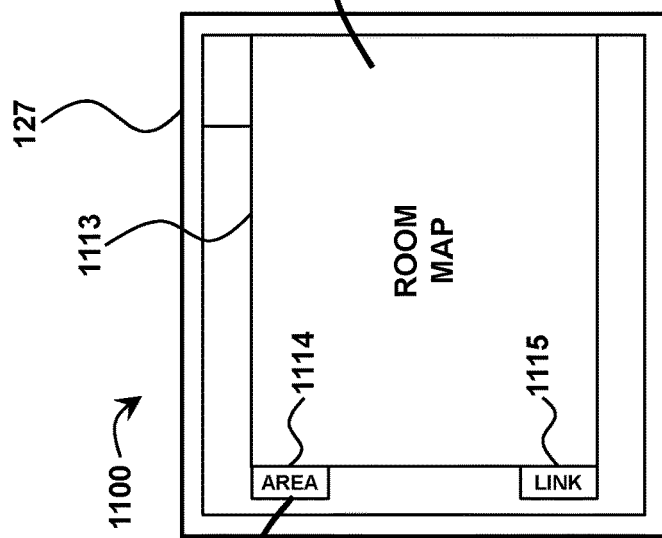
Figure 11C:
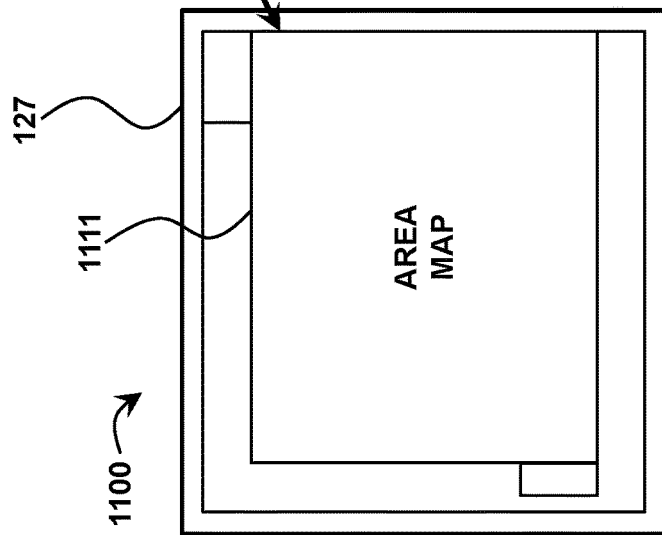

For use of device 180 in facilities 3 having numerous areas 7 and rooms 9, the map feature of device 180 provides the requisite number of area maps and room maps, along with corresponding sampling locations 1 in area(s) 7 and/or room(s) 9, to meet operational needs of users 15. FIGS. 11C-11E depict examples of an area map 1111, a room map 1113, and an annotated room map 1116 having sampling location(s) 1 displayed concurrently therewith.

User 15 may cause, via processor 103, the GUI 1100 to display the area map 1111 from a facility map view by, for example, interacting with graphics 1102 on the GUI 1100, as described above with reference to FIGS. 11A and 11B. Area map 1111 facilitates user 15 navigation to particular room(s) 9 in the area 7. Upon reaching the desired room 9, user 15 may cause, via processor 103, GUI 1100 to display the room map 1113 from the area map 1111 view by for example, interacting with the first drop down list 1103a shown and described above with reference to FIG. 11B. In an example, processor 103 causes GUI 1100 to display a link button 1115 concurrently with the room map 1113. In the example, upon entering the respective room 9, and with the room map 1113 being displayed to user 15, user 15 may cause, via processor 103, GUI 1100 to display the annotated room map 1116 by touching and/or otherwise interacting with GUI 1100 to actuate the link button 1115. In another example, user 15 may cause, via processor 103, GUI 1100 to display the annotated room map 1116 using the actions and sequencing of processor 103 steps shown in FIG. 11B and described above with reference to the second drop down list 1103b. In an embodiment, processor 103 causes GUI 1100 to display an area button 1114 concurrently with the room map 1113. In the example, user 15 may cause, via processor 103, GUI 1100 to display the area map 1111 and, optionally, to stop displaying the room map 1113, by touching and/or otherwise interacting with GUI 1100 to actuate the area button 1114. Similarly, processor 103 may cause GUI 1100 to display a room button 1117 and, optionally, the area button 1114, concurrently with the annotated room map 1116. In an embodiment, user 15 may cause, via processor 103, GUI 1100 to display the room map 1111 and, optionally, to stop displaying the annotated room map 1116, by touching and/or otherwise interacting with GUI 1100 to actuate the room button 1117.

FIG. 11F illustrates an example a multi-location sampling and/or analysis listing 1119 displayed on GUI 1100 as text and/or graphical indicators. In an embodiment, listing 1119 provides a plurality of sampling location 1 indicators. In an embodiment, listing 1119 is included in, and displayed via processor 103 operations to user 15 on GUI 1100 as, a drop down listing. In another embodiment, listing 1119 occupies all or part of display 127 on the GUI 1100. In an example, processor 103 causes listing 1119 to be displayed on GUI 1100 concurrently with map button 1109, which may include the same or similar functionality as shown and described above with reference to FIG. 11B. In a use case, user 15 may utilize listing 1119 on GUI 1100 to catalog and/or otherwise record and keep track of progress in sampling- and/or analysis-related tasks and completion status thereof for multiple sampling locations 1 in a particular room 9. In an example, the textual and/or graphical indicator corresponding to respective sampling location(s) 1 having been sampled and/or analyzed by, for example and without limitation, device 180, are caused to be displayed by processor 103 on GUI 1100 in listing 1119 with a changed appearance (e.g., highlighted, bolded, starred, circled, etc.) upon their being completed and upon their respective sample data being stored by processor 103 in memory 105 in association with their respective unique identifiers including the sampling location 1.

Figure 12A:
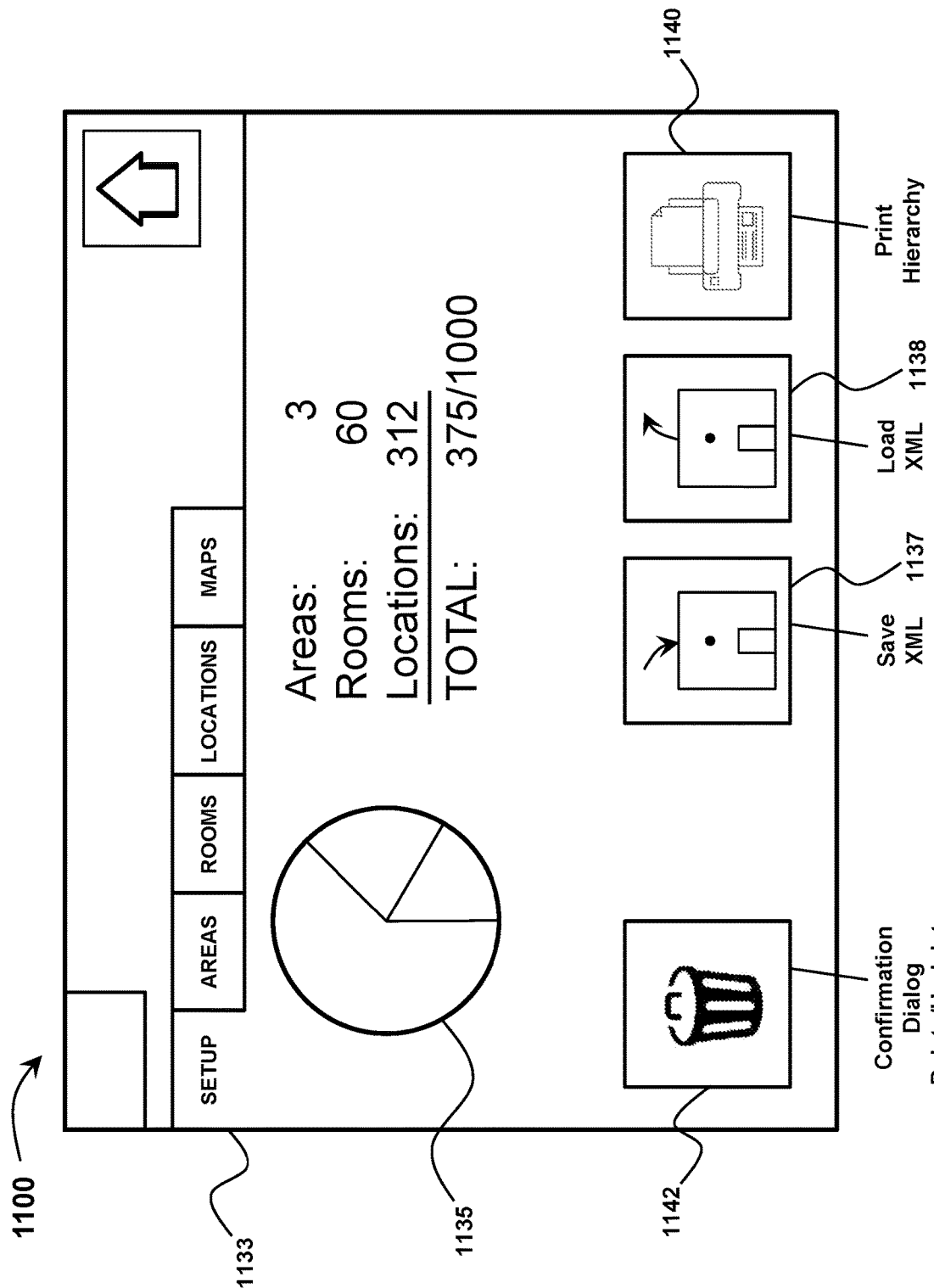
FIGS. 12A-12F illustrate screens of the device GUI and a web-based tool for use in configuring device map features with requisite spatial tiers along with sampling location(s), according to some embodiments of the disclosure.

FIGS. 12A-12F illustrate configuration screens of the device 180 GUI 1100 and a web-based tool for use in configuring device 180 map features with requisite spatial tiers (e.g., facility 3, area(s) 7, and room(s) 9) along with sampling location(s) 1, according to some embodiments of the disclosure. FIG. 12A shows a setup tab 1133. Tab 1133 provides user 15 overall control of the location features of device 180, as shown and described above with reference to FIGS. 11A-11F. In an embodiment, processor 103 causes an indication (e.g., a pie chart 1135, representing, for instance, a number of locations (e.g., area(s) 7, room(s) 9, and/or sampling location(s) 1 of facility 3) that may be stored in memory 105. Thus, in the example illustrated in FIG. 12A, memory 105 may store a total of 1000 such locations, and tab 1133 shows, via pie chart 1135, that 375 of them are currently being used, leaving 625 available to user 15. Processor 103 may cause one or more buttons to be displayed on GUI 1100 in tab 1133 User 15 touching a save button 1137 on GUI 1100 causes processor 103 to save location configuration files in memory 105. User 15 touching a load button 1138 on GUI 1100 causes processor 103 to load location configuration files from memory 105. User 15 touching a print button 1140 on GUI 1100 causes processor 103 to provide data to an attached printer to print a hierarchy of spatial data (e.g., map images with or without sampling location(s) 1) for facility 3 and/or a hierarchical listing of sampling location(s) 1 therein. User 15 touching a delete button 1142 on GUI 1100 causes processor 103 to display a confirmation dialog box graphic (not shown in FIG. 12A) which, when confirmed by user 15, causes processor to delete configuration files from memory 105.

Figure 12B:
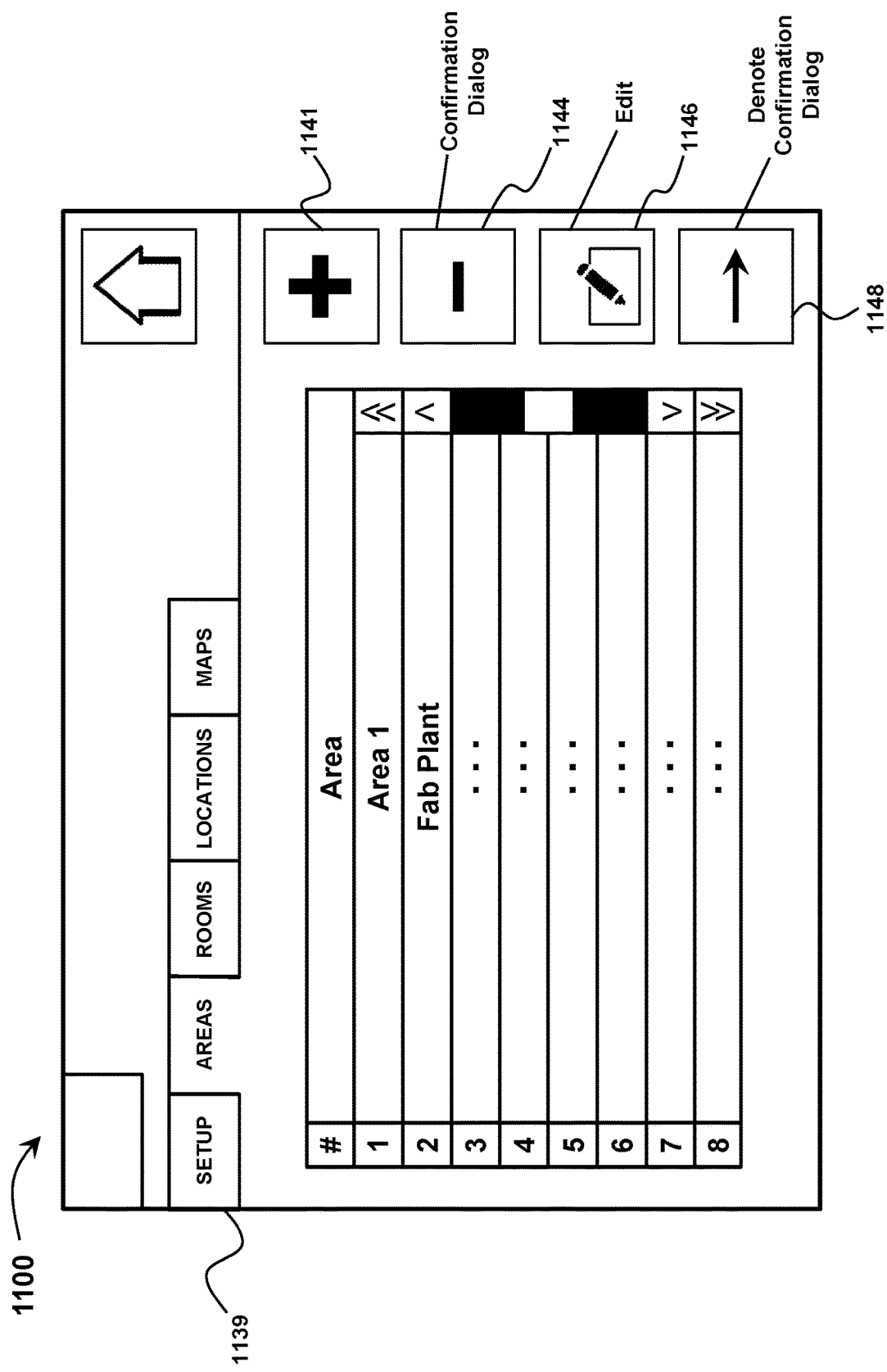

FIG. 12B shows a textual configuration tab 1139. Tab 1139 enables user 15 to configure text to be displayed on maps and other features of GUI 1100 and/or to be stored as metadata for unique identifier(s) in association with sample data, as described above with reference to method 200. Processor 103 may cause one or more buttons to be displayed on GUI 1100 in tab 1139. User 15 touching an add button 1141 on GUI 1100 causes processor 103 to add a spatial tier and/or sampling location 1 to be made available for user 15 textual configuration. User 15 touching a remove button 1144 on GUI 1100 causes processor 103 to display a confirmation dialog box graphic (not shown in FIG. 12B) which, when confirmed by user 15, causes processor to delete a prior configured spatial tier and/or sampling location 1 from memory 105. User 15 touching an edit button 1146 on GUI 1100 causes processor 103 to open a prior configured spatial tier and/or sampling location 1 to be made available from memory 105 for editing by user 15. After being so edited, user 15 touching a confirmation button 1148 causes processor 103 to open an edit confirmation dialog box (not shown in FIG. 12B) which, when confirmed by user 15, causes processor 103 to save the edited textual configuration file in memory 105.

Figure 12C:
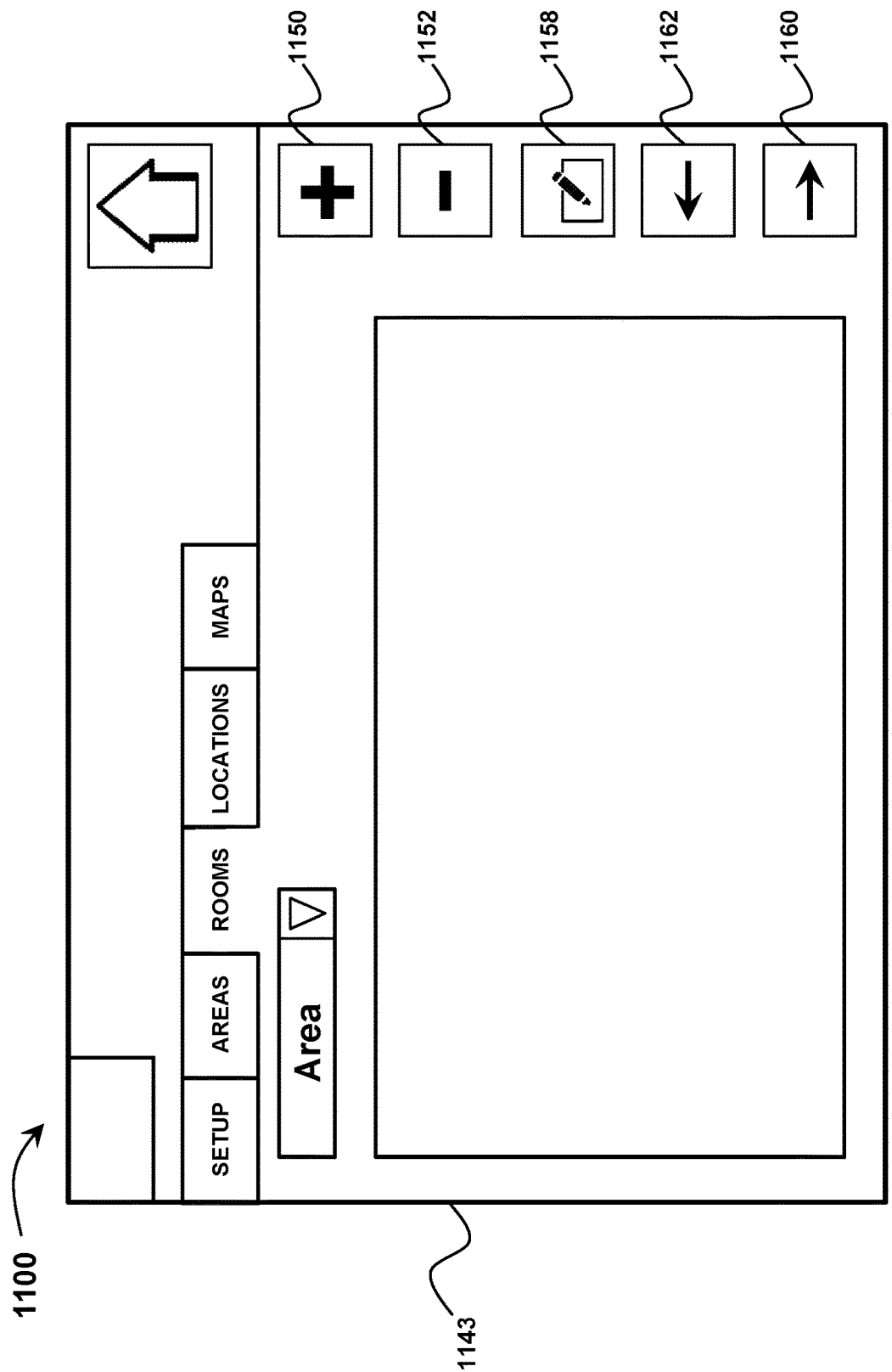

FIG. 12C shows a map configuration tab 1143. Tab 1143 enables user 15 to configure the map features of device 180. For example, tab 1143 is employed by user 15 to add room(s) 9 to area 7 map(s). Processor 103 may cause one or more buttons to be displayed on GUI 1100 in tab 1143. User 15 touching an add button 1150 on GUI 1100 causes processor 103 to add a map file to be made available for user 15 configuration. User 15 touching a remove button 1152 on GUI 1100 causes processor 103 to display a confirmation dialog box graphic (not shown in FIG. 12C) which, when confirmed by user 15, causes processor to delete a prior configured map file from memory 105. User 15 touching an edit button 1158 on GUI 1100 causes processor 103 to open a prior configured map file to be made available from memory 105 for editing by user 15. After being so edited, user 15 touching a confirmation button 1160 causes processor 103 to open an edit confirmation dialog box (not shown in FIG. 12C) which, when confirmed by user 15, causes processor 103 to save the edited map file in memory 105. User 15 touching an undo button 1162 on GUI 1100 causes processor 103 to revert back to the prior stored configured map file thus undoing any changes made to it.

Figure 12D:
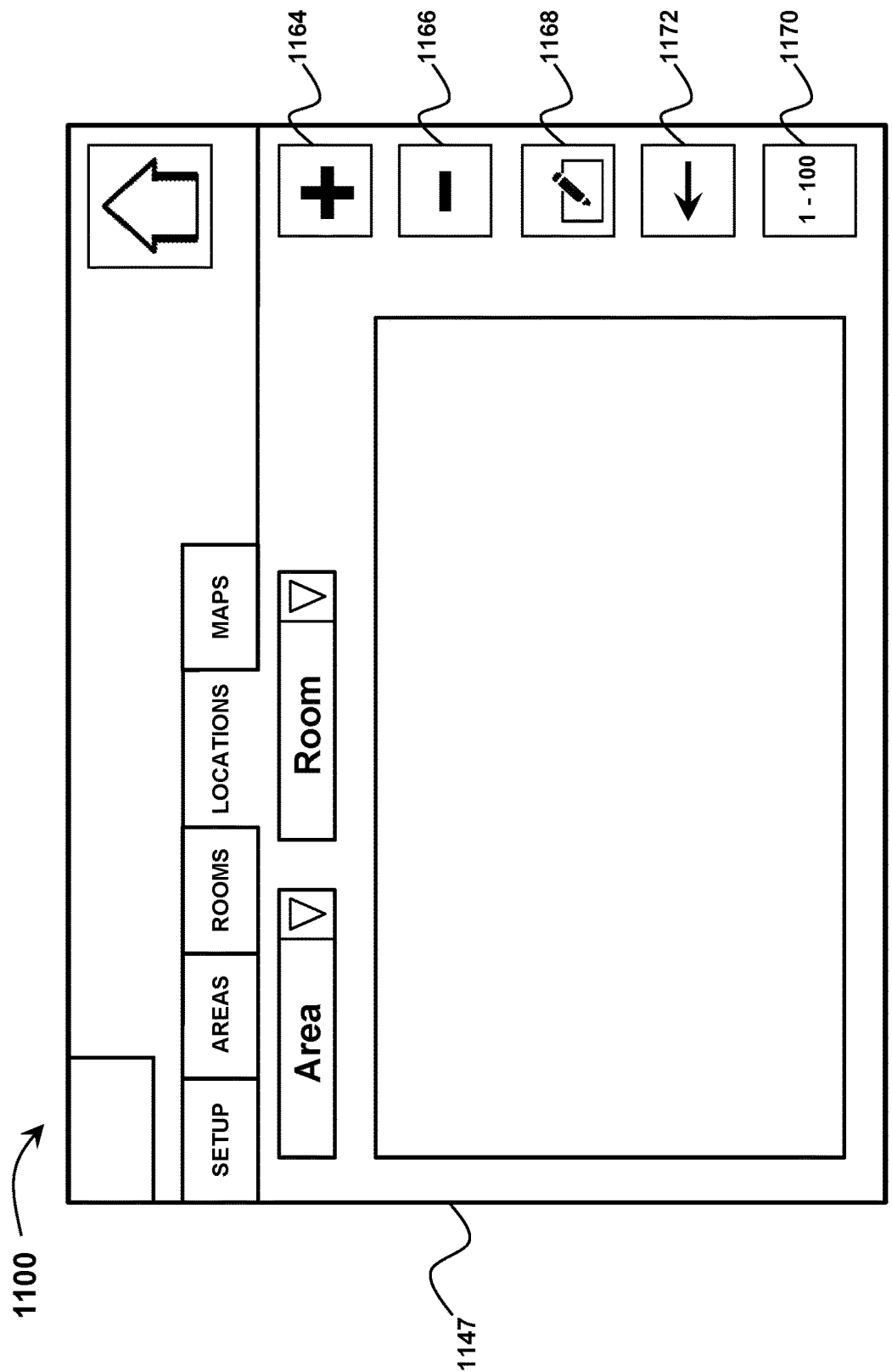

FIG. 12D shows a sampling location configuration tab 1147. Tab 1147 enables user 15 to add locations to a specific spatial tier maps of facility 3. For example, tab 1143 is employed by user 15 to add sampling location(s) 1 to a specific room 9 within a defined area 7. Processor 103 may cause one or more buttons to be displayed on GUI 1100 in tab 1147. User 15 touching an add button 1164 on GUI 1100 causes processor 103 to add a map file to be made available for user 15 configuration. User 15 touching a remove button 1166 on GUI 1100 causes processor 103 to display a confirmation dialog box graphic (not shown in FIG. 12D) which, when confirmed by user 15, causes processor to delete a prior configured sampling location 1 from memory 105. User 15 touching an edit button 1168 on GUI 1100 causes processor 103 to open a prior configured sampling location 1 file to be made available from memory 105 for editing by user 15. After being so edited, user 15 touching an auto-populate button 1170 causes processor 103 to automatically create a plurality of names of sampling locations 1 (e.g., "Location 001," "Location 002," etc.) for a particular room 9. User 15 touching an undo button 1172 on GUI 1100 causes processor 103 to revert back to the prior stored configured sampling location 1 file thus undoing any changes made to it.

Figure 12E:
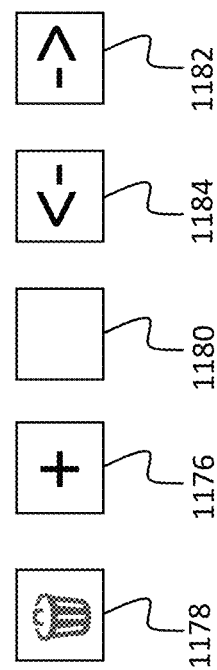
Figure 12F:
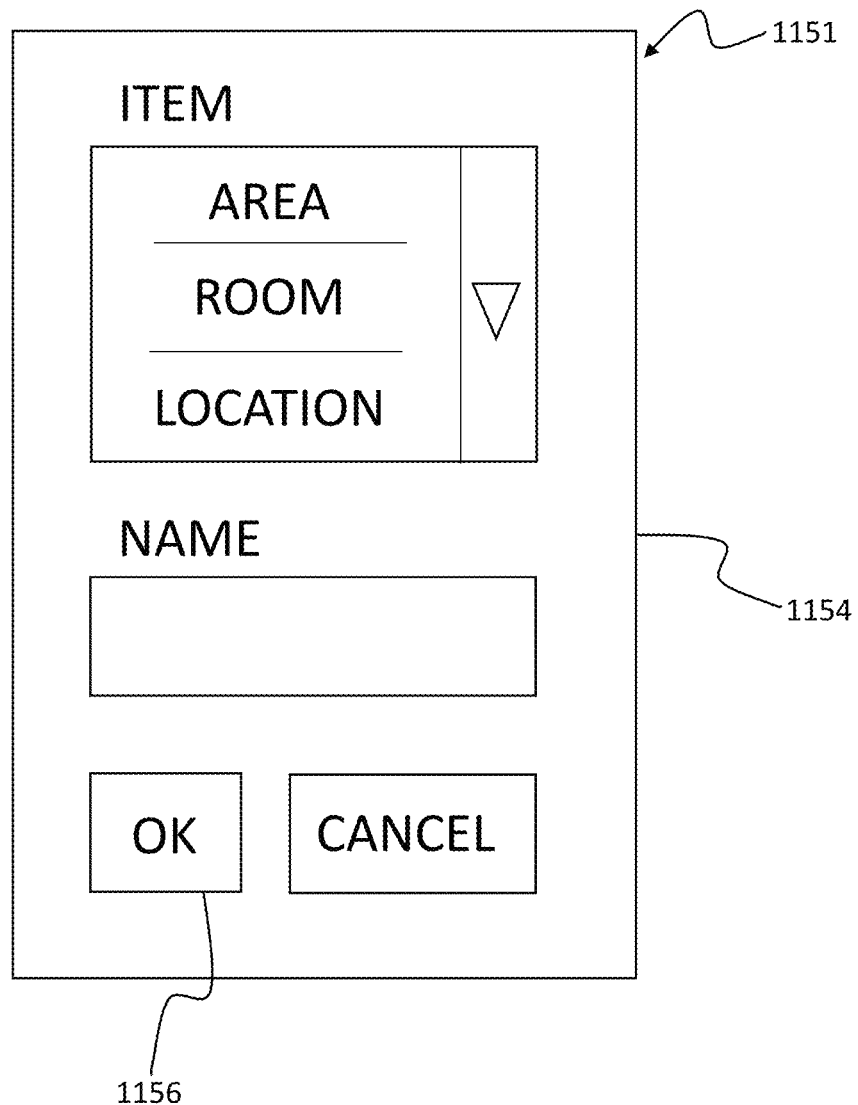

FIG. 12E shows a Web page interface 1151 for device 180. Interface 1151 enables user 15 to edit the names of area(s) 7, room(s) 9, and sampling location(s) 1 within a facility 3. Interface 1151 provides the same or similar functionality as GUI 1100, but user 15 is able to emulate, for example, textual configuration tab 1139, and/or configure additional or other various features of device 180, as described above, but without having the device 180 in hand. For instance, web interface 1151 may include buttons. User 15 clicking on interface 1151 at an add button 1176 causes interface 1151 to add a spatial tier and/or sampling location 1 to be made available for user 15 textual configuration. User 15 clicking on interface 1151 at a remove button 1178 causes interface 1151 to display a confirmation dialog box graphic (not shown in FIG. 12E) which, when confirmed by user 15, causes processor 103 to delete a prior configured spatial tier and/or sampling location 1 from memory 105. User 15 clicking on interface 1151 at an edit button 1180 causes processor 103 to open and display, via interface 1151, a prior configured spatial tier and/or sampling location 1 to be made available from memory 105 for editing by user 15. After being so edited, user 15 clicking on interface 1151 at a confirmation button 1182 causes interface 1151 to open an edit confirmation dialog box (not shown in FIG. 12E) which, when confirmed by user 15, causes processor 103 to save the edited textual configuration file in memory 105. User 15 clicking on interface 1151 at an undo button 1184 causes processor 103 to revert back to the prior stored configured map file thus undoing any changes made to it. FIG. 12F shows a pop-up dialog 1154 on interface 1151 for adding a location. Pull down menus of areas and rooms are provided. The user 15 selects the area, then the room, then types in a location name and clicks an OK button 1156, which causes this new location is added to the chosen room and area.

Figure 13:
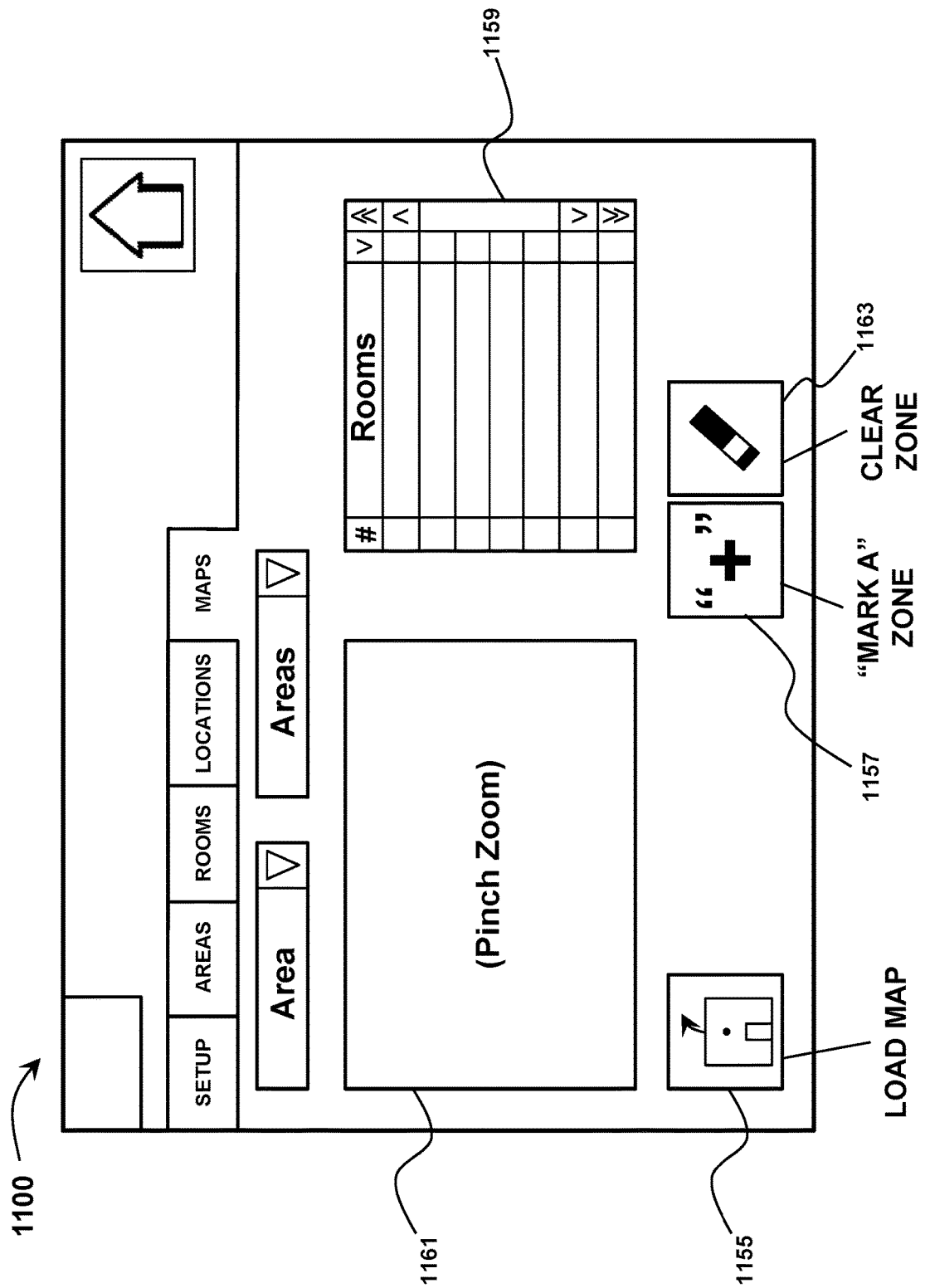
FIG. 13 illustrates a screen of the device GUI for use in additional aspects of configuring and editing the device map features, according to an embodiment of the disclosure.

FIG. 13 illustrates a screen of the device 180 GUI 1100 for use in additional aspects of configuring and editing the device 180 map features, according to an embodiment of the disclosure. FIG. 13 further illustrates how maps are loaded and configured on the instrument (e.g., device 180). FIG. 13 illustrates how an area map may be loaded onto device 180 and then configured with touch-points for rooms 9. A JPG or PNG image file of the area 7 is loaded via the "Load Map" button 1155. In an example, the user 15 loads an externally generated file onto the device 180 via a USB FLASH key (or a file is loaded via the browser interface 1151 implementation). To add Rooms to the area map, first a mark zone button 1157 button is touched. Then a Room is selected (i.e. touched) from the named list 1159 on the right side of the GUI 1100 screen. Finally, an appropriate location on the map 1161 on the left side of the GUI 1100 screen is touched. A Clear Zone button 1163 is provided to unmark a zone on the map.

FIGS. 14-17 illustrate examples the device 180 GUI 1100 and/or web-based interfaces and tools for use in additional aspects operation of device 180, including configuring and editing the device 180 map features, according to some embodiments of the disclosure.

Figure 14:
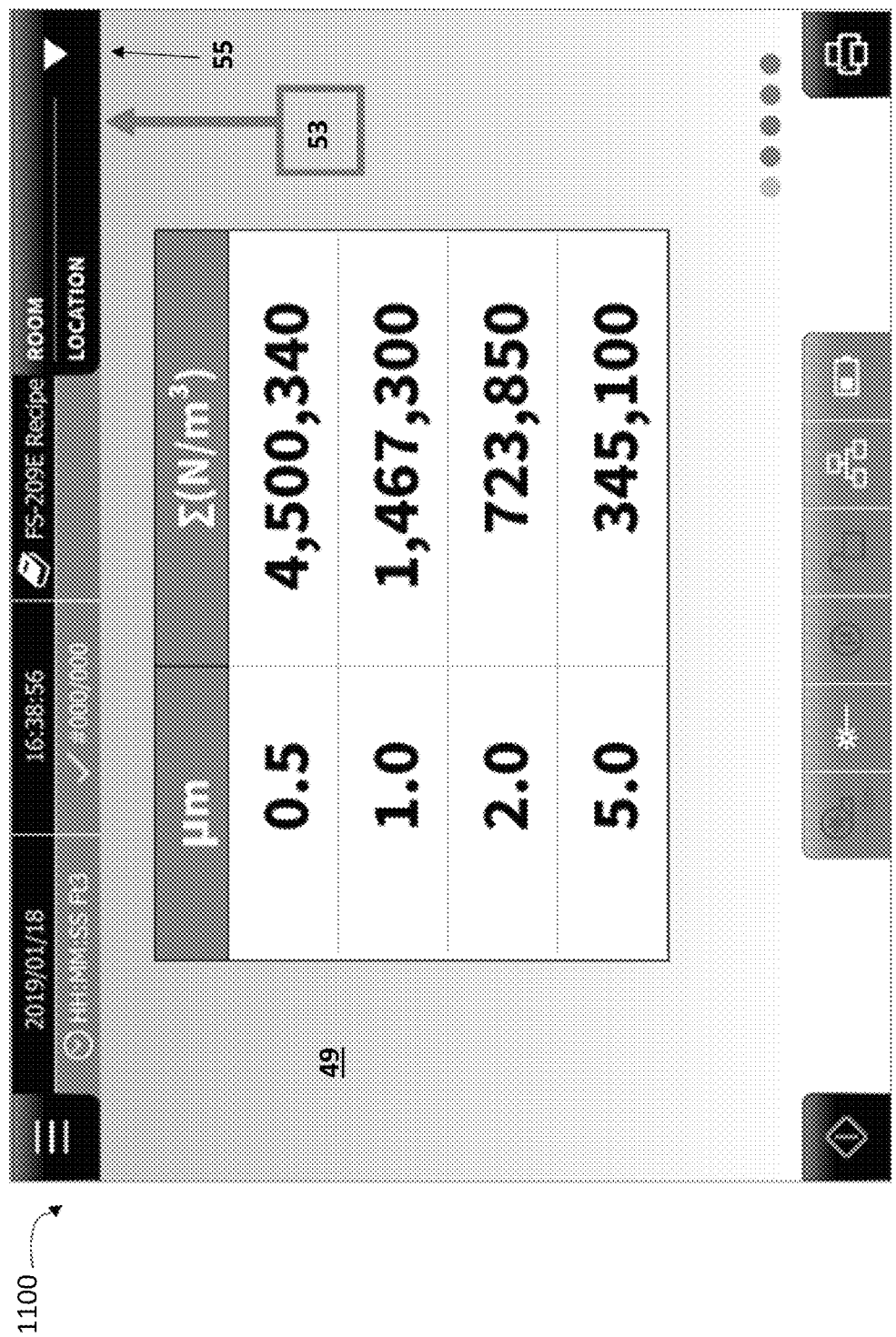
FIGS. 14-17 illustrate examples the device GUI and/or web-based interface and tools for use in additional aspects operation of device, including configuring and editing the device map features, according to some embodiments of the disclosure.

Referring to FIG. 14, a main screen 49 of the GUI 1100 may include a pull-down location selector graphic 53. In one embodiment, graphic 53 is displayed in a form and/or operates in the same or similar manner, as graphic 1102, as shown and described above with reference to FIG. 11A. In the example shown in FIG. 14 graphic 53 In a closed state shows the current room 9 and sampling location 1 within that room 9. When user 15 touches or otherwise interacts with the arrow 55 displayed in GUI 1100, this causes the GUI 1100 to open a pair of list boxes (not shown in FIG. 14) with functionality allowing user 15 to select the area 7, room 9, and sampling location(s) 1 in either a text form or via displayed maps including, without limitation, those shown and described above with reference to FIGS. 1 and 3. In one embodiment, the aforementioned list boxes displayed by GUI 1100 upon user 15 touching or otherwise interacting with arrow 55 are displayed in a form and/or operate in the same or similar manner, as first 1103*a* and/or second 1103*b* drop down lists, as shown and described above with reference to FIG. 11B.

Figure 15:
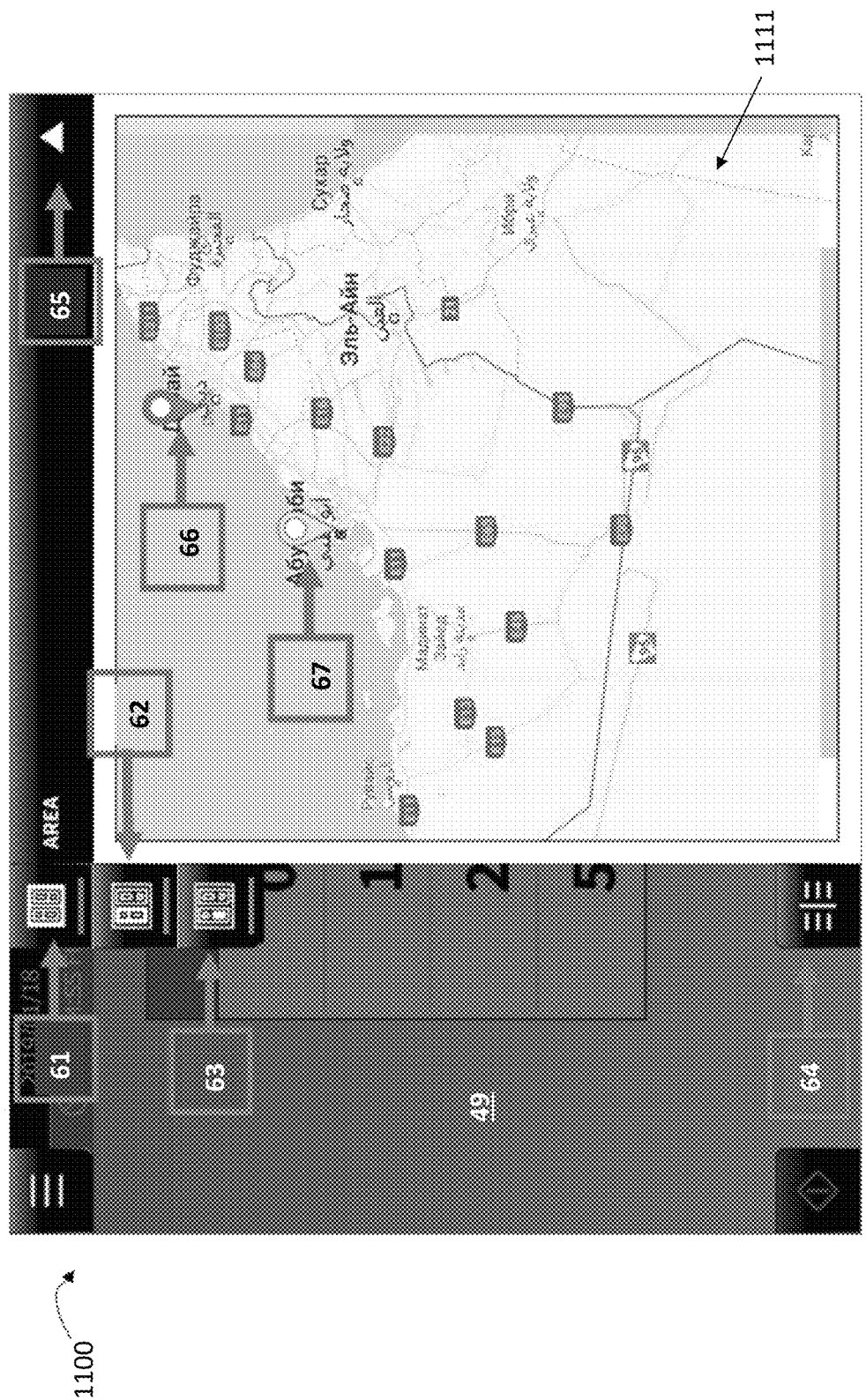
Figure 16:
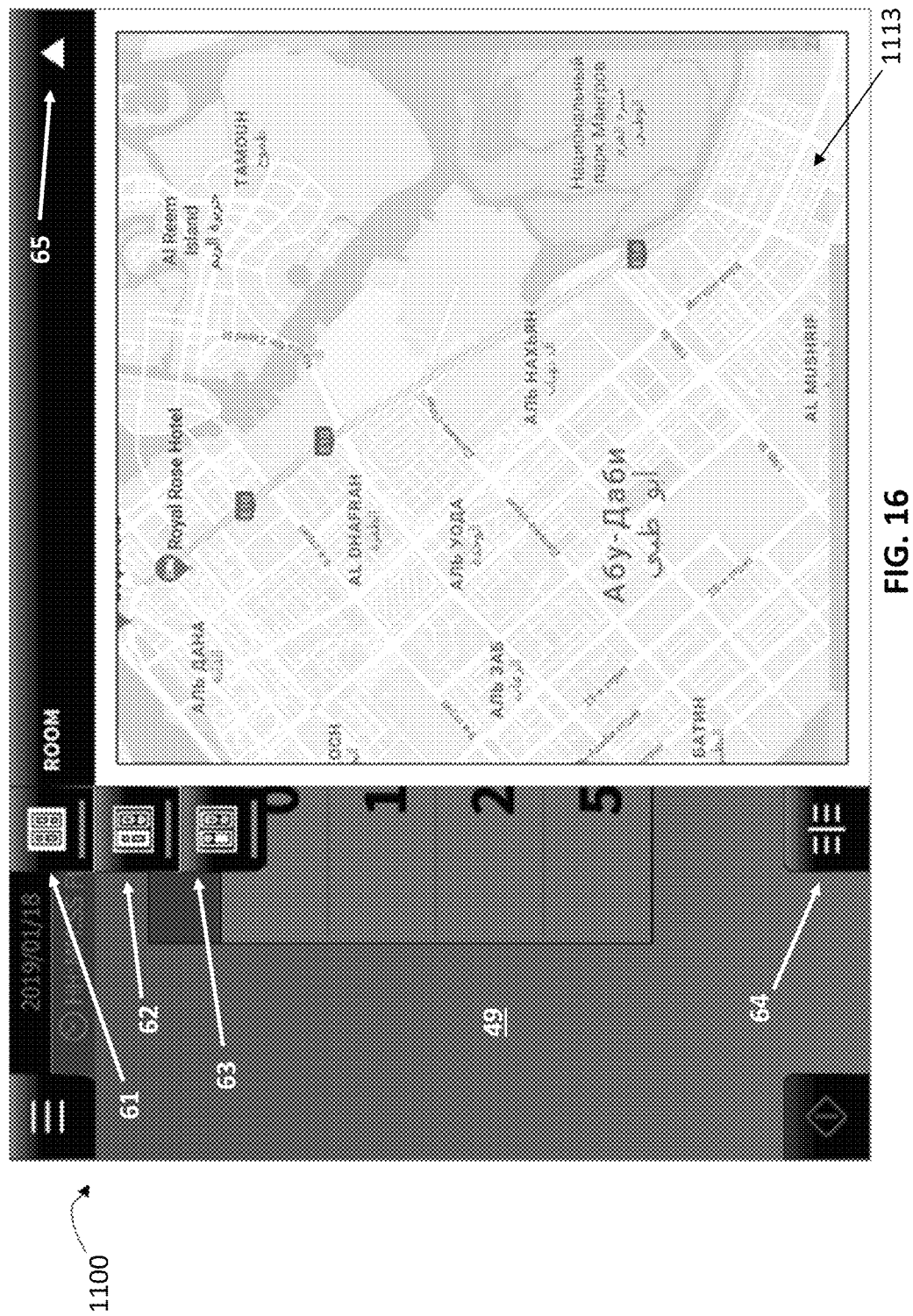

Referring to FIG. 15, the main screen 49 of the GUI 1100 may include an area selection button 61 for selecting an area 7. In one embodiment, user 15 touching or otherwise interacting with button 61 causes GUI 1100 to display the area map 1111 corresponding to the selection of user 15. Main screen 49 may include a room selection button 62. In an embodiment, user 15 touching or otherwise interacting with button 62 causes GUI 1100 to display the room map 1113 corresponding to the selection of user 15. Main screen 49 may include a sampling location 1-level selection button 63. In one embodiment, user 15 touching or otherwise interacting with button 63 causes GUI 1100 to display the annotated room map 1116 corresponding to the selection of user 15. The resulting changes in the example GUI 1100 shown in FIG. 15 are illustrated, by way of example, in FIG. 16. A similar change in how GUI 1100 is displayed occurs upon user touching and/or otherwise interacting with button 63.

The main screen 49 shown in FIG. 15 may include a toggle button 64 for enabling user 15 to toggle between maps views and list views (e.g., drop down list(s) 1103*a* and/or 1103*b*). In an example, toggle button 64 includes graphics displayed as an icon in the form of a map when the GUI 1100 is currently displaying a list view. In the example, toggle button 64 includes graphics displayed as an icon in the form of a list when the GUI 1100 is currently displaying a map view. User 15 touching or otherwise interacting with toggle button 64 causes GUI 1100 to alternately display the map view and the list view corresponding to the map view.

The main screen 49 shown in FIG. 15 may include a screen selection button 65 for enabling user 15 to toggle between map and/or list view(s) and the main screen 49 view depicted, for example, in FIG. 14. User 15 touching or otherwise interacting with screen selection button 65 causes GUI 1100 to alternately display the map and/or list view and the main screen 49 view without overlain map and/or list view(s). In one embodiment, in cases in which a recipe is associated with a room 9 and/or sampling location 1, selecting the pin icon 66 to convert it to a selected pin icon 67 further causes processor 103 to load that recipe from memory 103.

The main screen 49 shown in FIG. 15 may include a map pin icon 66 concurrently displayed by GUI 1100 with one or more of the map views. In an example, user 15 touching and/or otherwise interacting with map pin icon(s) 66 causes GUI 1100 to change a color and/or otherwise change the displayed appearance of, the map pin icon(s) 66. In an embodiment, user 15 touching and/or otherwise interacting with map pin icon(s) 66 converts the map pin icon(s) 66 into selected map pin icon(s) 67. In one embodiment, user 15 touching or otherwise interacting with map pin icon(s) 66 further causes the sampling location(s) 1 corresponding to the selected map pin icon(s) 67 to undergo appearance alteration in listing 1119 and further causes the additional processing and storing steps to be performed by processor 103 and memory 105, as shown and described above with reference to FIG. 11F.

Figure 17:
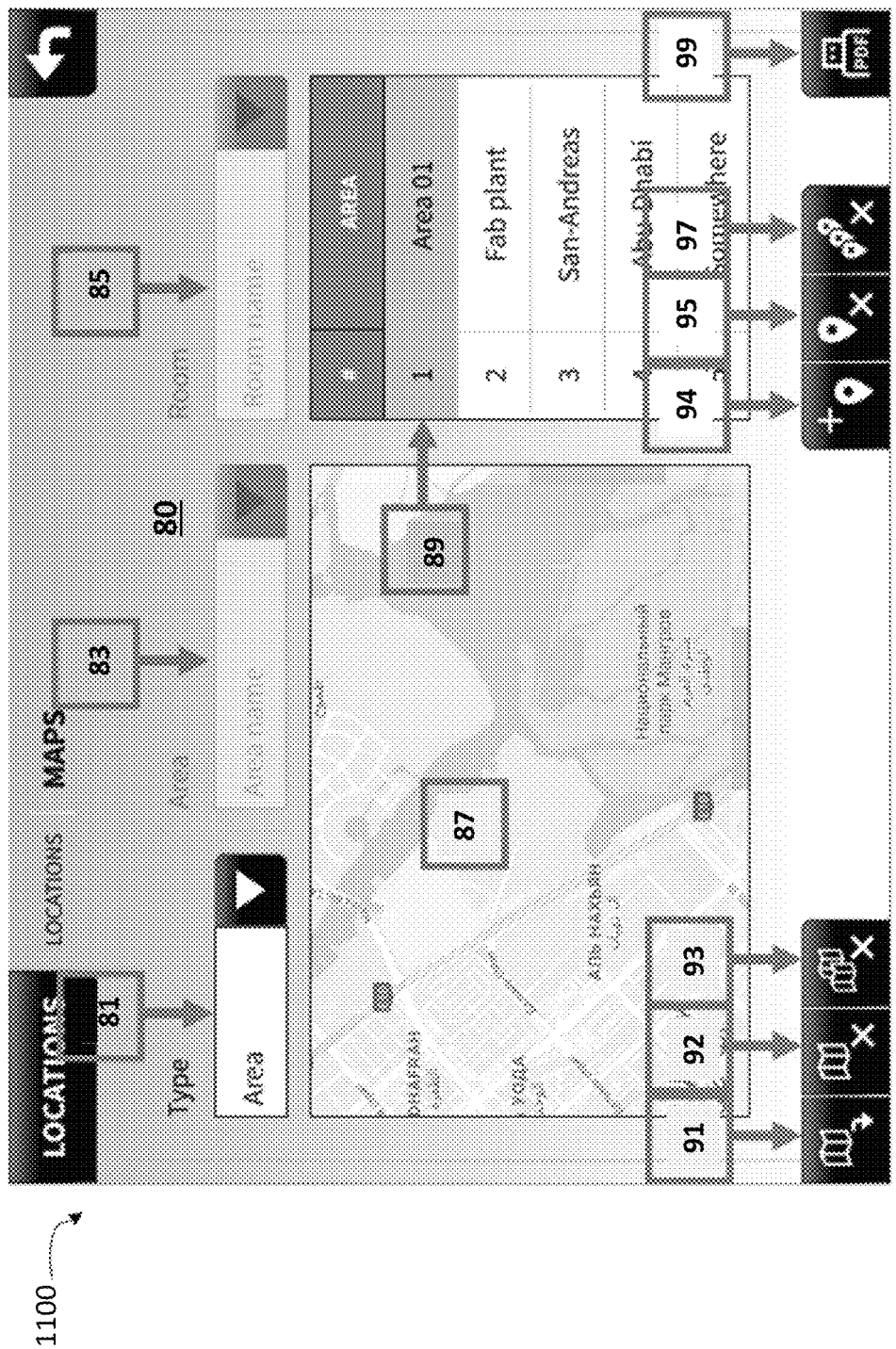

Referring to FIG. 17, GUI 1100 may include a map editing screen 80. Map editing screen 80 includes a type selection drop-down list 81. Selections available for the user 15 to touch or otherwise interact with in type selection drop-down list 81 include Area, Room or Location. When set to Area, the Facility level map may be added, deleted or edited. When set to Room, then one of several maps which allow selecting adding, deleting or editing room will be displayed. When set to Location, then same capability is provided for maps that have location selections. Map editing screen 80 includes an area name selection drop-down list 83. When the selection type (e.g., from drop down list 81) is Area, this control is disabled. When the selection type is Room or Location, then drop-down list 83 allows selecting an Area. Map editing screen 80 includes a room name selection drop-down list 85. When the selection type (e.g., from drop down list 81) is Area or Room, this control is disabled. When the selection type is Location, then drop-down list 85 allows selecting a Room.

Map editing screen 80 includes a select map display area 87. If no map has been loaded from memory 105, a blank region is shown on display 127. When the selection type (e.g., from drop down list 81) is Area, then the Facility level map may be added, deleted or edited. When the selection type (e.g., from drop down list 81) is Room, then an Area map with Rooms on it may be added, deleted or edited. When the selection type (e.g., from drop down list 81) is Location, then a Room map with Locations may be added, deleted or edited.

Map editing screen 80 includes a named selection list 89. This list 89 is populated with either Area names, Room names or Location names. The population type matches the Type selection drop-down (e.g., from drop down list 81). The items in this list 89 are the existing names which may be "pinned" to points on the appropriate map (e.g., pin icon(s) 66, as shown and described above with reference to FIG. 15). A single selection is provided in the list 89. The selected item may be pinned to the map (see description of map pin button 94, below).

Map editing screen 80 includes a load map button 91. Upon user 15 touching or otherwise interacting with button 91, button 91 enables user 15 to upload a map to the system (e.g., device 180) from memory 103. In an example, the map file is loaded by processor 103 from a USB FLASH key memory 105 form. In other examples, additional and/or other external file interfaces and/or memory 105 forms for map files may be utilized, as described by way of example above with reference to Example 3. Once loaded by processor 103 from memory 105, the map will be displayed by GUI 1100 as described above with reference to select map display area 87. If a map is already loaded by processor 103 from memory 105 for the selection, then button 91 may be disabled.

Map editing screen 80 includes a remove map button 92. Upon user 15 touching or otherwise interacting with button 92, button 92 enables user 15 to cause GUI 1100 to stop displaying the currently selected map. In an example, GUI 1100 displays a pop-up window (not shown in FIG. 17) on display 127 to confirm the user's 15 desire to remove the map and GUI 1100 stops displaying the currently selected map only in response to user 15 touching or otherwise interacting with this pop-up window in manner indicative of user's 15 desire to remove the currently selected map from GUI 1100. Map editing screen 80 includes a remove all maps button 93. Upon user 15 touching or otherwise interacting with button 93, button 93 enables user 15 to cause GUI 1100 to stop displaying all maps loaded by processor 103 from memory 105 on display 127. In an example, GUI 1100 displays a pop-up window (not shown in FIG. 17) on display 127 to confirm the user's 15 desire to remove all maps and GUI 1100 stops displaying all the maps only in response to user 15 touching or otherwise interacting with this pop-up window in manner indicative of user's 15 desire to remove all maps from GUI 1100 on display 127.

Map editing screen 80 includes a map pin button 94. Upon user 15 touching or otherwise interacting with button 94, button 94 enables user 15 to cause GUI 1100 to display graphics in the form of a pin on the respective for the highlighted and/or otherwise selected item in the Named Selection list 89. The point touched and/or otherwise selected via GUI 1100 interaction by user 15 on the map after pressing button 94 will be assigned the current Named Selection. Each selection point on the map will show a pin icon 66. Therefore, in the embodiment, adding selections to the map is a three step process. First user 15 selects a Name (e.g., from Named Selection list 89). Second, user 15 presses the map pin button 94. Finally, user 15 touches the select map display area 87 at the desired point. A new map pin icon 66 is displayed on GUI 1100 once this is done.

Map editing screen 80 includes a map unpin button 95. Upon user 15 touching or otherwise interacting with button 95, button 95 enables user 15 to cause GUI 1100 to stop displaying the map pin icon 66 corresponding to the currently selected item in the Named Selection list 89. In an example, GUI 1100 displays a pop-up window (not shown in FIG. 17) on display 127 to confirm the user's 15 desire to remove the respective map pin icon 66 from select map display area 87 and GUI 1100 stops displaying that map pin icon 66 only in response to user 15 touching or otherwise interacting with this pop-up window in manner indicative of user's 15 desire to remove the respective map pin icon 66.

Map editing screen 80 includes a map unpin all button 97. Upon user 15 touching or otherwise interacting with button 97, button 97 enables user 15 to cause GUI 1100 to stop displaying all map pin icons 66 in the select map display area 87. In an example, GUI 1100 displays a pop-up window (not shown in FIG. 17) on display 127 to confirm the user's 15 desire to remove all the map pin icons 66 in the select map display area 87 and GUI 1100 stops displaying all the map pin icons 66 only in response to user touching or otherwise interacting with this pop-up window in manner indicative of user's 15 desire to remove all the map pin icons 66 in maps from GUI 1100 on display 127.

Map editing screen 80 includes a Print Map PDF report button 99. Upon user 15 touching or otherwise interacting with button 99, button 99 enables user 15 to cause processor 103 to generate and, optionally, store in memory 105 and/or direct transmission of, a PDF report for the at least one of the maps configured as described, by way of example, above. In one embodiment, the PDF report includes images of all maps in the system embedded in the PDF report file including selection points (e.g., map pin icons 66), and a list of the selection point names (e.g., the Area 7, Room 9, and/or Sampling Location 1 names).

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art.

As used herein, "comprising" is synonymous with "including," "containing," "having," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of operating a portable particle sampling device, the method comprising the steps of:
sampling an environment at a sampling location with the device; and
associating the sampling location with a unique identifier, wherein the unique identifier comprises an area and the sampling location;
selecting the area;
displaying a sampling location associated with the selected area on a graphical user interface (GUI) connected to the device;
receiving an indication that the device has arrived at the sampling location;
in response to the indication, loading a decvice recipe for at least one of: particle sampling, and particle analysis;
executing the device recipe via the device; and
in response to the device executing the device recipe, strong sample data for the sampling location in association with: the unique identifier, and an identifier of the device recipe.

2. The method of claim 1, further comprising:
providing the device to a user tasked with the sampling of a facility at the sampling location,
wherein the facility has a plurality of spatial tiers including: the area, and a room.

3. The method of claim 2, further comprising:
receiving a request from the user for spatial data for one of the plurality of spatial tiers of the facility; and
in response to the request, displaying the spatial data to the user to facilitate the user navigating to the sampling location.

4. A method of operating a portable particle sampling device, the method comprising the steps of:
sampling an environment at a sampling location with the device; and
associating the sampling location with a unique identifier, wherein the unique identifier comprises an area and the sampling location;
selecting the area;
displaying a sampling location associated with the selected area on a graphical user interface (GUI) connected to the device;
providing the device to a user tasked with the sampling of a facility at the sampling location;
wherein the facility has a plurality of spatial tiers including: the area, and a room;
receiving a request from the user for spatial data for one of the plurality of spatial tiers of the facility;
in response to the request, displaying the spatial data to the user to facilitate the user navigating to the sampling location; and
loading a sampling plan routine corresponding to the sampling of the facility by the user, wherein the device is provided to the user pre-loaded with the sampling plan routine.

5. The method of claim 4, wherein the sampling plan routine includes the spatial data of the facility.

6. The method of claim 3, wherein the request from the user is received via the GUI.

7. The method of claim 3, wherein displaying the spatial data to the user includes causing responsive spatial data to be displayed as a graphical map to the user.

8. A method of operating a portable particle sampling device, the method comprising the steps of:
sampling an environment at a sampling location with the device; and
associating the sampling location with a unique identifier, wherein the unique identifier comprises an area and the sampling location;
selecting the area;
displaying a sampling location associated with the selected area on a graphical user interface (GUI) connected to the device;
providing the device to a user tasked with the sampling of a facility at the sampling location;
wherein the facility has a plurality of spatial tiers including: the area, and a room;
receiving a request from the user for spatial data for one of the plurality of spatial tiers of the facility;
in response to the request, displaying the spatial data to the user to facilitate the user navigating to the sampling location; and
loading a sampling plan routine corresponding to the sampling of the facility by the user, wherein the device is provided to the user pre-loaded with the sampling plan routine.

9. The method of claim 8, wherein the spatial data includes one or more graphical maps for one or more of the plurality of spatial tiers of the facility.

10. The method of claim 7, wherein causing responsive spatial data to be displayed as a graphical map to the user includes displaying a graphical map of the room, and wherein the graphical map includes the sampling location.

11. The method of claim 1, further comprising causing one or more user instructions to be displayed, to the user, as a portion of the GUI.

12. The method of claim 1, wherein the indication is received from the user via the GUI.

13. A method of operating a portable particle sampling device, the method comprising the steps of:
sampling an environment at a sampling location with the device; and
associating the sampling location with a unique identifier, wherein the unique identifier comprises an area and the sampling location;
selecting the area;
displaying a sampling location associated with the selected area on a graphical user interface (GUI) connected to the device;
receiving an indication that the device has arrived at the sampling location; and
in response to the indication, loading a device recipe for at least one of: particle sampling, and particle analysis;
wherein loading the device recipe includes loading the recipe according to the sampling location corresponding to the indication received.

14. The method of claim 1, further comprising transmitting the sample data from the device to a location remote from the device for at least one of: monitoring, and archiving, of the sample data.

15. A method of operating a portable particle sampling device, the method comprising the steps of:
   sampling an environment at a sampling location with the device; and
   associating the sampling location with a unique identifier, wherein the unique identifier comprises an area and the sampling location;
   selecting the area;
   displaying a sampling location associated with the selected area on a graphical user interface (GUI) connected to the device;
   providing the device to a user tasked with the sampling of a facility at the sampling location;
   wherein the facility has a plurality of spatial tiers including: the area, and a room;
   receiving a request from the user for spatial data for one of the plurality of spatial tiers of the facility;
   in response to the request, displaying the spatial data to the user to facilitate the user navigating to the sampling location; and
   wherein the device further comprises a first device and at least a second device, the method further comprising exporting at least one of: the spatial data of the facility, a device recipe, and an identifier of the user, from the first to the at least a second device.

16. The method of claim 1, wherein the unique identifier further comprises a room.

\* \* \* \* \*

UNITED STATES PATENT AND TRADEMARK OFFICE
CERTIFICATE OF CORRECTION

PATENT NO. : 11,416,123 B2
APPLICATION NO. : 16/394931
DATED : August 16, 2022
INVENTOR(S) : Daniele Pandolfi et al.

Page 1 of 1

It is certified that error appears in the above-identified patent and that said Letters Patent is hereby corrected as shown below:

In the Claims

In Column 36, in Claim 8, Lines 32-33, please delete "a sampling plan routine corresponding to the sampling of the facility by the user" and replace with – the spatial data corresponding to the plurality of spatial tiers of the facility –.

In Column 36, in Claim 8, Line 35, please delete "plan routine" and replace with – spatial data –.

Signed and Sealed this
Twentieth Day of December, 2022

Katherine Kelly Vidal
*Director of the United States Patent and Trademark Office*